United States Patent
Salih et al.

(10) Patent No.: US 12,398,208 B2
(45) Date of Patent: *Aug. 26, 2025

(54) PSMA BINDING ANTIBODY AND USES THEREOF

(71) Applicants: Deutsches Krebsforschungszentrum Stiftung des Öffentlichen Rechts, Heidelberg (DE); EBERHARD KARLS UNIVERSITÄT TÜBINGEN, Tübingen (DE)

(72) Inventors: Helmut Salih, Stuttgart (DE); Fabian Vogt, Tübingen (DE); Gundram Jung, Rottenburg (DE); Latifa Zekri-Metref, Tübingen (DE)

(73) Assignees: Deutsches Krebsforschungszentrum Stiftung Des Öffentlichen Rechts, Heidelberg (DE); Eberhard Karls Universität Tübingen, Tübingen (DE)

( * ) Notice: Subject to any disclaimer, the term of this patent is extended or adjusted under 35 U.S.C. 154(b) by 79 days.

This patent is subject to a terminal disclaimer.

(21) Appl. No.: 17/934,232

(22) Filed: Sep. 22, 2022

(65) Prior Publication Data

US 2023/0132249 A1   Apr. 27, 2023

Related U.S. Application Data

(62) Division of application No. 16/069,656, filed as application No. PCT/EP2017/050834 on Jan. 16, 2017, now Pat. No. 11,612,646.

(30) Foreign Application Priority Data

Jan. 14, 2016 (EP) ..................................... 16151281

(51) Int. Cl.
| | |
|---|---|
| C07K 16/28 | (2006.01) |
| A61K 39/00 | (2006.01) |
| A61P 35/00 | (2006.01) |
| C07K 16/30 | (2006.01) |

(52) U.S. Cl.
CPC .. *C07K 16/2809* (2013.01); *A61K 39/001194* (2018.08); *A61K 39/001195* (2018.08); *A61P 35/00* (2018.01); *C07K 16/3069* (2013.01); *C07K 16/3084* (2013.01); *A61K 2039/572* (2013.01); *A61K 2039/884* (2018.08); *C07K 2317/24* (2013.01); *C07K 2317/31* (2013.01); *C07K 2317/55* (2013.01); *C07K 2317/622* (2013.01); *C07K 2317/73* (2013.01)

(58) Field of Classification Search
None
See application file for complete search history.

(56) References Cited

U.S. PATENT DOCUMENTS 11,612,646 B2   3/2023   Salih et al.

FOREIGN PATENT DOCUMENTS

| | | | |
|---|---|---|---|
| EP | 2155783 A2 | 2/2010 | |
| EP | 2155788 A2 | 2/2010 | |
| WO | WO-2003/080672 A1 | 10/2003 | |
| WO | WO-2010/037837 A2 | 4/2010 | |
| WO | WO-2013092001 A1 * | 6/2013 | ............. A61P 35/00 |
| WO | WO-2015/143033 A1 | 9/2015 | |
| WO | WO-2015/158868 A2 | 10/2015 | |

OTHER PUBLICATIONS

Arakawa et al., "Cloning and Sequencing of the VH and Vk Genes of an Anti-CD3 Monoclonal Antibody, and Construction of a Mouse/Human Chimeric Antibody," J Biochem, 120:657-662 (1996).
Buhler et al., "A bispecific diabody directed against prostate-specific membrane antigen and CD3 induces T-cell mediated lysis of prostate cancer cells," Cancer Immunology, Immunotherapy, 57(1):43-52 (2007).
Buhler et al., "Targer-dependent T-cell activation by coligation with a PSMA x CD3 diabody induces lysis of prostate cancer cells," Journal of Immunotherapy, 32(6_:567-572 (2009).
Chen et al., "Generation and Analysis of Random Point Mutations in an Antibody CDR2 Sequence: Many Mutated Antibodies Lose Their Ability to Bind Antigen," J Exp Med, 176: 855-866 (1992).
Dougan et al., "Effects of substitutions in the binding surface of an antibody on antigen affinity," Protein Eng. 11(1): 65-74 (1998).
Fortmuller et al., "Effective targeting of prostate cancer by lympocytes redirected by a PSMA * CD3 bispecific single-chain diabody," Prostate, Wiley-Liss, 71(6):588-596 (2011).
International Preliminary Report on Patentability for International Application No. PCT/EP2017/050834 mailed Jul. 26, 2018.
International Search Report and Written Opinion for International Application No. PCT/EP2017/050834 mailed May 30, 2017.
MacCallum et al., "Antibody-antigen Interactions: Contact Analysis and Binding Site Topography" J. Molecular Biology 262: 732-745 (1996).
Roitt et al., "Immunology," w/ English Translation, p. 151 (2000).
Rudikoff et al., "Single amino acid substitution altering antigen-binding specificity," PNAS, 79: 1979-1983 (1982).
Sela-Culang et al., "The strutcural basis of antibody-antigen recognition" Frontiers in Immunology 4(302): 13 pages (2013).
Sewell et al., "319 anti-PSMA X anti-CD3 bispecific antibody efficiently redirects T cells cytotoxicity in castrate-resistant prostate cancer models," European Journal of Cancer, 48(1):98 (2012).

(Continued)

*Primary Examiner* — Laura B Goddard
(74) *Attorney, Agent, or Firm* — Foley Hoag LLP; Susan M. Abelleira; Tatiana P. Headrick

(57) ABSTRACT

The present invention provides a novel PSMA binding antibody termed 10B3 and pharmaceutical and diagnostic uses of the antibody 10B3. The PSMA antibody 10B3 does not cross-compete with the state of the art PMSA binding antibody J591 and has a reduced induction of antigen shift compared to J591 and a unique reactivity with squamous cell carcinoma (SCC) cells of different origin.

5 Claims, 17 Drawing Sheets

Specification includes a Sequence Listing.

(56) References Cited

OTHER PUBLICATIONS

Tamura et al., "Structural correlates of an anticarcinoma antibody: identification of specificity-determining residues (SDRs) and development of a minimally immunogenic antibody variant by retention of SDRs only", the Journal of Immunology 164(3): 1432-1441 (2000).

* cited by examiner

Fabsc

IgGsc bssc

• Molecular weight standard

Fig. 5A: Binding
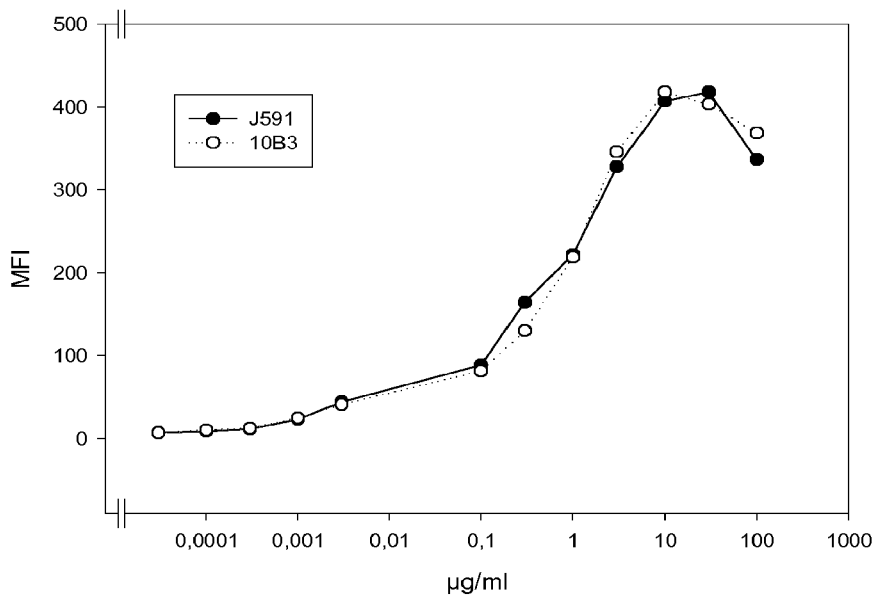
Fig. 5B: Competition of binding
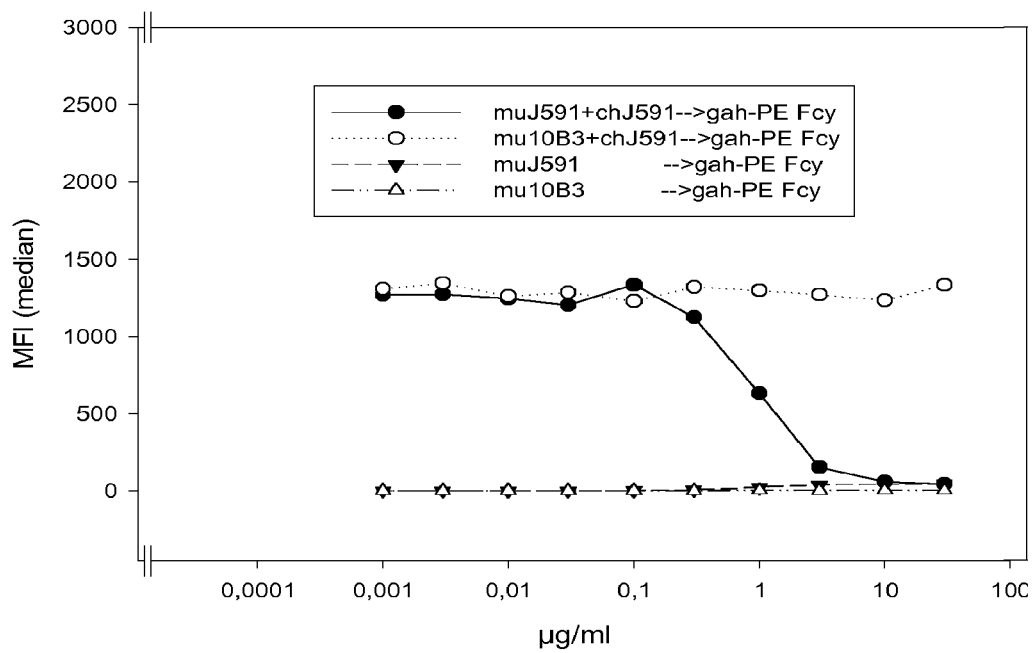

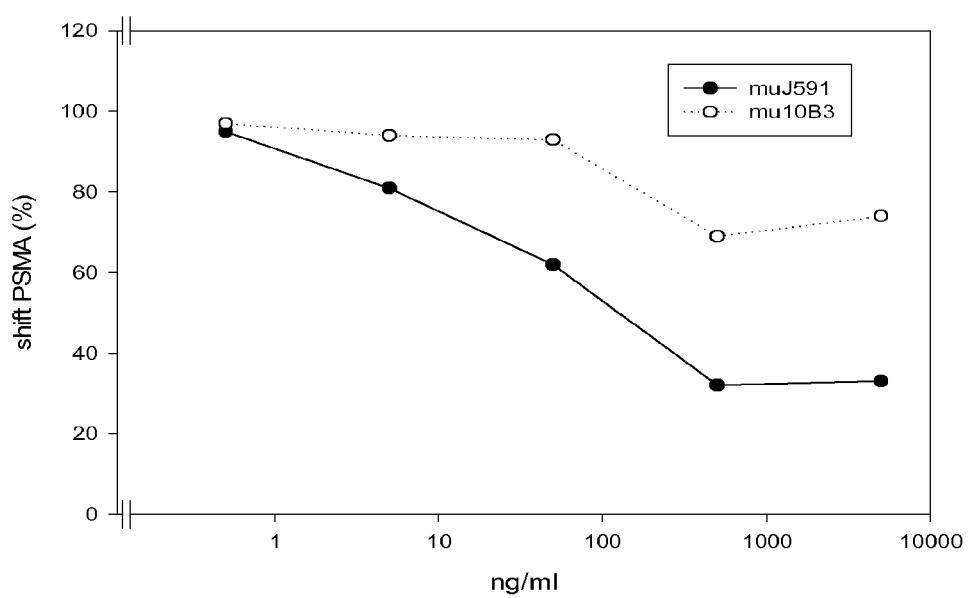
Fig. 5C: Antigen shift

FIG. 9

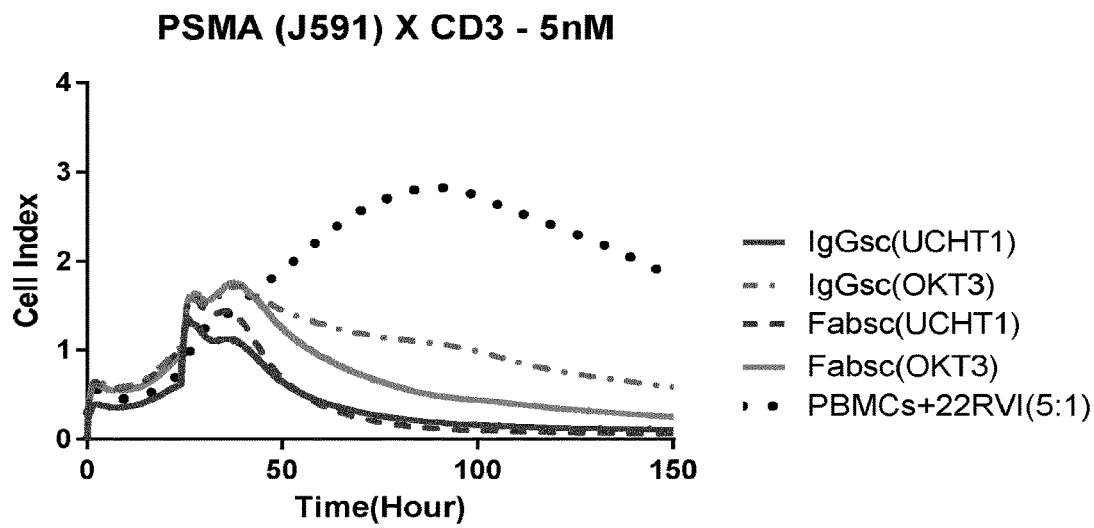

Fig. 10A: *PSMA (m10B3) murine HC variable region*

QVQLQESGGGLVKPGGSLKLSCAAS<u>GFTFSDFYMY</u>WVRQTPEKRLEWVA<u>TISDG
GGYTSYPDSVKG</u>RFTISRDIAKNNLYLQMNSLKSEDTAKYYCAR<u>GLWLRDALDY</u>W
GQGTSVTVSS
(SEQ ID NO: 01)

Fig. 10B: *PSMA (m10B3) murine LC variable region*

EIVLTQSPITMAAFLGERITITC<u>SASSSISSNYLH</u>WYQQKPGFSPKLLIY<u>RTSNLAS</u>GV
PIRFSGSGSGTSYSLTIGTMEAEDVATYYC<u>QQGSYIPFT</u>FGSGTKLEIKR
(SEQ ID NO: 02)

Fig.10C: *PSMA (h10B3) humanized HC variable region*

QVQLVESGGGLVKPGGSLRLSCAAS<u>GFTFSDFYMY</u>WIRQAPGKGLEWVA<u>TISDGG
GYTSYPDSVKG</u>RFTISRDNAKNSLYLQMNSLRAEDTAVYYCAR<u>GLWLRDALDY</u>WG
QGTTVTVSS
(SEQ ID NO: 09)

Fig.10D: *PSMA (h10B3) humanized LC variable region*

EIVLTQSPATLSLSPGERATLSC<u>SASSSISSNYLH</u>WYQQKPGQAPRLLIY<u>RTSNLAS</u>
GIPARFSGSGSGTD*Y*TLTISRLEPEDFAVYYC<u>QQGSYIPFT</u>FGQGTKLEIKR
(SEQ ID NO: 10)

FIG. 11

*IgGsc_PSMA (h10B3)_CD3 (hUCHT1) Heavy chain*

METDTLLLWVLLLWVPGSTGQVQLVESGGGLVKPGGSLRLSCAASGFTFSDFYMYWIRQA
Ig Leader peptide          Humanized PSMA (10B3) HC variable region PGKGLEWVATISDGGGYTSYPDSVKGRFTISRDNAKNSLYLQMNSLRAEDTAVYYCARGL
Humanized PSMA (10B3) HC variable region WLRDALDYWGQGTTVTVSSASTKGPSVFPLAPSSKSTSGGTAALGCLVKDYFPEPVTVSW
IgG1 CH1 domain NSGALTSGVHTFPAVLQSSGLYSLSSVVTVPSSSLGTQTYICNVNHKPSNTKVDKKVEPKSC
IgG1 CH1 domain DKTHTCPPCPAPPVAGPSVFLFPPKPKDTLMISRTPEVTCVVVGVSHEDPEVKFNWYVDGV
IgG1 hinge region          Mutated IgG1CH2 domain EVHNAKTKPREEQYNSTYRVVSVLTVLHQDWLNGKEYKCKVSNKQLPSPIEKTISKAKGQP
Mutated IgG1CH2 domain REPQVYTLPPSRDELTKNQVSLTCLVKGFYPSDIAVEWESNGQPENNYKTTPPVLDSDGSF
IgG1 CH3 domain

FLYSKLTVDKSRWQQGNVFSCSVMHEALHNHYTQKSLSLSPGKSGDIQMTQSPSSLSASV

GDRVTITCRASQDIRNYLNWYQQKPGKAPKLLIYYTSRLESGVPSRFSGSGSGTDYTLTISS
Humanized CD3 single chain (UCHT1) LC variable region LQPEDFATYYCQQGNTLPWTFGQGTKVEIKGGGGSGGGGSGGGGSEVQLVESGGGLVQ
Linker region PGGSLRLSCAASGYSFTGYTMNWVRQAPGKGLEWVALINPYKGVSTYNQKFKDRFTISVD
Humanized CD3 single chain (UCHT1) HC variable region

KSKNTAYLQMNSLRAEDTAVYYCARSGYYGDSDWYFDVWGQGTLVTVSS**

(SEQ ID NO: 11)

FIG. 12

*S6: Fabsc_PSMA (h10B3)_mCD3 (OKT3) Heavy chain*

METDTLLLWVLLLWVPGSTGQVQLVESGGGLVKPGGSLRLSCAASGFTFSDFYMYWIRQA
    Ig Leader peptide                            Humanized PSMA (10B3) HC variable region PGKGLEWVATISDGGGYTSYPDSVKGRFTISRDNAKNSLYLQMNSLRAEDTAVYYCARGL
                    Humanized PSMA (10B3) HC variable region WLRDALDYWGQGTTVTVSSASTKGPSVFPLAPSSKSTSGGTAALGCLVKDYFPEPVTVSW
                                IgG1 CH1 domain NSGALTSGVHTFPAVLQSSGLYSLSSVVTVPSSSLGTQTYICNVNHKPSNTKVDKKVEPKSC
                                IgG1 CH1 domain DKTHTSPPSPAPPVAGPSVFLFPPKPKDTLMISRTPEVTCVVVGVSHEDPEVKFNWYVDGV
    IgG1 hinge region                              Mutated IgG1CH2 domain EVHNAKTKPREEQYNSTYRVVSVLTVLHQDWLNGKEYKCKVSNKQLPSPIEKTISKAKGQP
                                                Beginning of IgG1 CH3 domain SGQVQLQQSGAELARPGASVKMSCKASGYTFTRYTMHWVKQRPGQGLEWIGYINPSRGY
                    CD3 single chain (OKT3) HC variable region

TNYNQKFKDKATLTTDKSSSTAYMQLSSLTSEDSAVYYCARYYDDHYCLDYWGQGTTLTVS

SGGGGSGGGGSGGGGSDIVLTQSPAIMSASPGEKVTMTCSASSSVSYMNWYQQKSGTSP
      Linker region

KRWIYDTSKLASGVPAHFRGSGSGTSYSLTISGMEAEDAATYYCQQWSSNPFTFGSGTKLE
                  CD3 single chain OKT3 LC variable region

IN**

(SEQ ID NO: 12)

FIG. 13

*PSMA (h10B3)_Kappa_ Light chain*

METDTLLLWVLLLWVPGSTGEIVLTQSPATLSLSPGERATLSCSASSSISSNYLHWYQQKPG
      Ig Leader peptide                     Humanized PSMA (10B3) LC variable region QAPRLLIYRTSNLASGIPARFSGSGSGTDYTLTISRLEPEDFAVYYCQQGSYIPFTFGQGTKL
               Humanized PSMA (10B3) LC variable region EIKRTVAAPSVFIFPPSDEQLKSGTASVVCLLNNFYPREAKVQWKVDNALQSGNSQESVTE
                         C-Kappa QDSKDSTYSLSSTLTLSKADYEKHKVYACEVTHQGLSSPVTKSFNRGEC**
                      C-Kappa (SEQ ID NO: 13)

Fig. 14A: *mPSMA (J591)HC variable region*

EVQLQQSGPELVKPGTSVRISCKTSGYTFTEYTIHWVKQSHGKSLEWIGNINPNNGGTTYN
QKFEDKATLTVDKSSSTAYMELRSLTSEDSAVYYCAAGWNFDYWGQGTTLTVSS (SEQ ID NO: 15)

Fig. 14B: *mPSMA (J591)LC variable region*

DIVMTQSHKFMSTSVGDRVSIICKASQDVGTAVDWYQQKPGQSPKLLIYWASTRHTGVPD
RFTGSGSGTDFTLAITNVQSEDLADYFCQQYNSYPLTFGAGTKLEIKR (SEQ ID NO: 16)

FIG. 15E
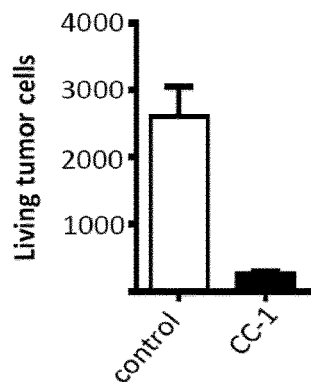
FIG. 15F
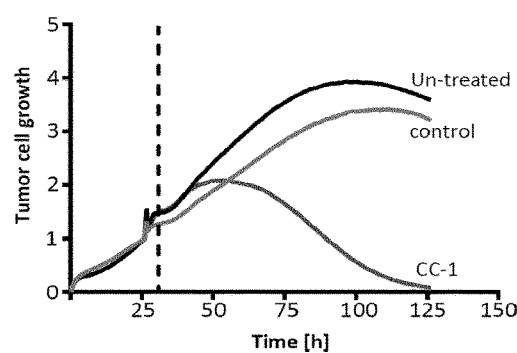 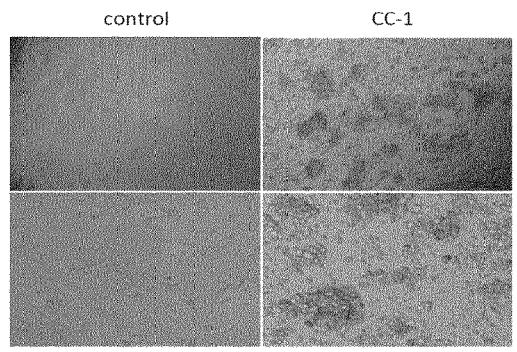
FIG. 16A
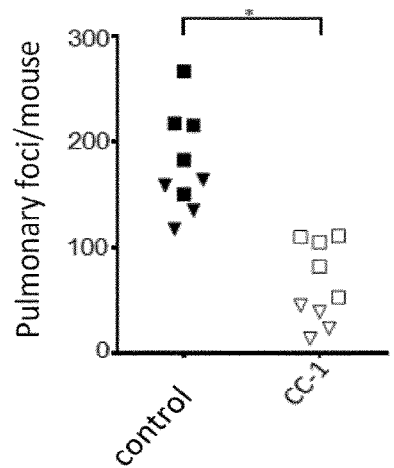

```
                       SEQUENCE LISTING

Sequence total quantity: 16
SEQ ID NO: 1            moltype = AA  length = 119
FEATURE                 Location/Qualifiers
REGION                  1..119
                        note = murine 10B3 antibody heavy chain variable region
source                  1..119
                        mol_type = protein
                        organism = synthetic construct
SEQUENCE: 1
QVQLQESGGG LVKPGGSLKL SCAASGFTFS DFYMYWVRQT PEKRLEWVAT ISDGGGYTSY    60
PDSVKGRFTI SRDIAKNNLY LQMNSLKSED TAKYYCARGL WLRDALDYWG QGTSVTVSS    119

SEQ ID NO: 2            moltype = AA  length = 109
FEATURE                 Location/Qualifiers
REGION                  1..109
                        note = murine 10B3 antibody light chain variable region
source                  1..109
                        mol_type = protein
                        organism = synthetic construct
SEQUENCE: 2
EIVLTQSPIT MAAFLGERIT ITCSASSSIS SNYLHWYQQK PGFSPKLLIY RTSNLASGVP    60
IRFSGSGSGT SYSLTIGTME AEDVATYYCQ QGSYIPFTFG SGTKLEIKR               109

SEQ ID NO: 3            moltype = AA  length = 10
FEATURE                 Location/Qualifiers
REGION                  1..10
                        note = CDR-H1 of 10B3 antibody
source                  1..10
                        mol_type = protein
                        organism = synthetic construct
SEQUENCE: 3
GFTFSDFYMY                                                          10

SEQ ID NO: 4            moltype = AA  length = 17
FEATURE                 Location/Qualifiers
REGION                  1..17
                        note = CDR-H2 of 10B3 antibody
source                  1..17
                        mol_type = protein
                        organism = synthetic construct
SEQUENCE: 4
TISDGGGYTS YPDSVKG                                                  17

SEQ ID NO: 5            moltype = AA  length = 10
FEATURE                 Location/Qualifiers
REGION                  1..10
                        note = CDR-H3 of 10B3 antibody
source                  1..10
                        mol_type = protein
                        organism = synthetic construct
SEQUENCE: 5
GLWLRDALDY                                                          10

SEQ ID NO: 6            moltype = AA  length = 12
FEATURE                 Location/Qualifiers
REGION                  1..12
                        note = CDR-L1 of 10B3 antibody
source                  1..12
                        mol_type = protein
                        organism = synthetic construct
SEQUENCE: 6
SASSSISSNY LH                                                       12

SEQ ID NO: 7            moltype = AA  length = 7
FEATURE                 Location/Qualifiers
```

```
REGION                       1..7
                             note = CDR-L2 of 10B3 antibody
source                       1..7
                             mol_type = protein
                             organism = synthetic construct
SEQUENCE: 7
RTSNLAS                                                                        7

SEQ ID NO: 8                 moltype = AA   length = 9
FEATURE                      Location/Qualifiers
REGION                       1..9
                             note = CDR-L3 of 10B3 antibody
source                       1..9
                             mol_type = protein
                             organism = synthetic construct
SEQUENCE: 8
QQGSYIPFT                                                                      9

SEQ ID NO: 9                 moltype = AA   length = 119
FEATURE                      Location/Qualifiers
REGION                       1..119
                             note = humanized 10B3 antibody heavy chain variable region
source                       1..119
                             mol_type = protein
                             organism = synthetic construct
SEQUENCE: 9
QVQLVESGGG LVKPGGSLRL SCAASGFTFS DFYMYWIRQA PGKGLEWVAT ISDGGGYTSY    60
PDSVKGRFTI SRDNAKNSLY LQMNSLRAED TAVYYCARGL WLRDALDYWG QGTTVTVSS    119

SEQ ID NO: 10                moltype = AA   length = 109
FEATURE                      Location/Qualifiers
REGION                       1..109
                             note = humanized 10B3 antibody light chain variable region
source                       1..109
                             mol_type = protein
                             organism = synthetic construct
SEQUENCE: 10
EIVLTQSPAT LSLSPGERAT LSCSASSSIS SNYLHWYQQK PGQAPRLLIY RTSNLASGIP    60
ARFSGSGSGT DYTLTISRLE PEDFAVYYCQ QGSYIPFTFG QGTKLEIKR               109

SEQ ID NO: 11                moltype = AA   length = 714
FEATURE                      Location/Qualifiers
REGION                       1..714
                             note = heavy chain of h10B3xhUCHT1 bispecific IgGsc format
                              antibody
source                       1..714
                             mol_type = protein
                             organism = synthetic construct
SEQUENCE: 11
METDTLLLWV LLLWVPGSTG QVQLVESGGG LVKPGGSLRL SCAASGFTFS DFYMYWIRQA    60
PGKGLEWVAT ISDGGGYTSY PDSVKGRFTI SRDNAKNSLY LQMNSLRAED TAVYYCARGL   120
WLRDALDYWG QGTTVTVSSA STKGPSVFPL APSSKSTSGG TAALGCLVKD YFPEPVTVSW   180
NSGALTSGVH TFPAVLQSSG LYSLSSVVTV PSSSLGTQTY ICNVNHKPSN TKVDKKVEPK   240
SCDKTHTCPP CPAPPVAGPS VFLFPPKPKD TLMISRTPEV TCVVVGVSHE DPEVKFNWYV   300
DGVEVHNAKT KPREEQYNST YRVVSVLTVL HQDWLNGKEY KCKVSNKQLP SPIEKTISKA   360
KGQPREPQVY TLPPSRDELT KNQVSLTCLV KGFYPSDIAV EWESNGQPEN NYKTTPPVLD   420
SDGSFFLYSK LTVDKSRWQQ GNVFSCSVMH EALHNHYTQK SLSLSPGKSG DIQMTQSPSS   480
LSASVGDRVT ITCRASQDIR NYLNWYQQKP GKAPKLLIYY TSRLESGVPS RFSGSGSGTD   540
YTLTISSLQP EDFATYYCQQ GNTLPWTFGQ GTKVEIKGGG GSGGGGSGGG GSEVQLVESG   600
GGLVQPGGSL RLSCAASGYS FTGYTMNWVR QAPGKGLEWV ALINPYKGVS TYNQKFKDRF   660
TISVDKSKNT AYLQMNSLRA EDTAVYYCAR SGYYGDSDWY FDVWGQGTLV TVSS         714

SEQ ID NO: 12                moltype = AA   length = 606
FEATURE                      Location/Qualifiers
REGION                       1..606
                             note = heavy chain of h10B3xOKT3 bispecific Fabsc format
                              antibody
source                       1..606
                             mol_type = protein
                             organism = synthetic construct
SEQUENCE: 12
METDTLLLWV LLLWVPGSTG QVQLVESGGG LVKPGGSLRL SCAASGFTFS DFYMYWIRQA    60
PGKGLEWVAT ISDGGGYTSY PDSVKGRFTI SRDNAKNSLY LQMNSLRAED TAVYYCARGL   120
WLRDALDYWG QGTTVTVSSA STKGPSVFPL APSSKSTSGG TAALGCLVKD YFPEPVTVSW   180
NSGALTSGVH TFPAVLQSSG LYSLSSVVTV PSSSLGTQTY ICNVNHKPSN TKVDKKVEPK   240
SCDKTHTSPP SPAPPVAGPS VFLFPPKPKD TLMISRTPEV TCVVVGVSHE DPEVKFNWYV   300
DGVEVHNAKT KPREEQYNST YRVVSVLTVL HQDWLNGKEY KCKVSNKQLP SPIEKTISKA   360
KGQPSGQVQL QQSGAELARP GASVKMSCKA SGYTFTRYTM HWVKQRPGQG LEWIGYINPS   420
RGYTNYNQKF KDKATLTTDK SSSTAYMQLS SLTSEDSAVY YCARYYDDHY CLDYWGQGTT   480
```

```
LTVSSGGGGS GGGGSGGGGS DIVLTQSPAI MSASPGEKVT MTCSASSSVS YMNWYQQKSG  540
TSPKRWIYDT SKLASGVPAH FRGSGSGTSY SLTISGMEAE DAATYYCQQW SSNPFTFGSG  600
TKLEIN                                                            606

SEQ ID NO: 13           moltype = AA  length = 235
FEATURE                 Location/Qualifiers
REGION                  1..235
                        note = light chain of humanized 10B3 antibody
source                  1..235
                        mol_type = protein
                        organism = synthetic construct
SEQUENCE: 13
METDTLLLWV LLLWVPGSTG EIVLTQSPAT LSLSPGERAT LSCSASSSIS SNYLHWYQQK  60
PGQAPRLLIY RTSNLASGIP ARFSGSGSGT DYTLTISRLE PEDFAVYYCQ QGSYIPFTFG  120
QGTKLEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC      235

SEQ ID NO: 14           moltype = AA  length = 10
FEATURE                 Location/Qualifiers
REGION                  1..10
                        note = mutated CDR-H1 of 10B3 antibody
source                  1..10
                        mol_type = protein
                        organism = synthetic construct
SEQUENCE: 14
GFSFTDFYMY                                                         10

SEQ ID NO: 15           moltype = AA  length = 115
FEATURE                 Location/Qualifiers
REGION                  1..115
                        note = variable heavy chain domain of J519 antibody
source                  1..115
                        mol_type = protein
                        organism = synthetic construct
SEQUENCE: 15
EVQLQQSGPE LVKPGTSVRI SCKTSGYTFT EYTIHWVKQS HGKSLEWIGN INPNNGGTTY  60
NQKFEDKATL TVDKSSSTAY MELRSLTSED SAVYYCAAGW NFDYWGQGTT LTVSS      115

SEQ ID NO: 16           moltype = AA  length = 108
FEATURE                 Location/Qualifiers
REGION                  1..108
                        note = variable light chain domain Jof J519 antibody
source                  1..108
                        mol_type = protein
                        organism = synthetic construct
SEQUENCE: 16
DIVMTQSHKF MSTSVGDRVS IICKASQDVG TAVDWYQQKP GQSPKLLIYW ASTRHTGVPD  60
RFTGSGSGTD FTLAITNVQS EDLADYFCQQ YNSYPLTFGA GTKLEIKR              108
```

PSMA BINDING ANTIBODY AND USES THEREOF

RELATED APPLICATIONS

This application is a divisional of U.S. application Ser. No. 16/069,656, filed Jul. 12, 2018, which is the U.S. National Stage of International Application No. PCT/EP2017/050834, filed Jan. 16, 2017, which designates the U.S., published in English, and claims priority under 35 U.S.C. §§ 119 or 365(c) to European Application No. 16151281.9, filed on Jan. 14, 2016. The entire teachings of the above applications are incorporated herein by reference.

INCORPORATION BY REFERENCE OF SEQUENCE LISTING

This application contains a Sequence Listing which has been submitted electronically in the ST.26 (.XML) format and is hereby incorporated by reference in its entirety.
File name: "ASN-00402 Sequence Listing.XML"; created Sep. 8, 2022; 23,485 bytes in size.

FIELD OF THE INVENTION

The present invention provides a novel PSMA binding antibody. The PSMA antibody of the invention does not cross-compete with the state of the art PMSA binding antibody J591 and has a reduced induction of antigen shift compared to J591 and a unique reactivity with squamous cell carcinoma (SCC) cells of different origin. Further, the present invention relates to a bispecific PSMAxCD3 antibody molecule. The present invention also relates methods for producing the antibody molecule of the invention as well as nucleic acids, vectors, and host cells. The invention further relates to methods of treating or diagnosing a disease using a PMSA antibody molecule of the invention.

BACKGROUND

Scientific work starting in the 1980ies has established that bispecific antibodies directed to a tumor associated antigen (TAA) and the T cell receptor (TCR)/CD3-complex are capable of activating T cells resulting in the lysis of TAA expressing tumor cells by the activated T cells (Staerz et al. Nature 1985, 314:628-631; Perez et al. Nature 1985, 316: 354-356; Jung et al. Proc Natl Acad Sci USA 1986, 83:4479-4483) Since CD3-antibodies, bound to Fc receptors (FcRs) via their Fc-part, are exceedingly efficient in inducing T cell activation and cytokine release as unwanted side effects, it is of paramount importance to construct Fc-depleted or -attenuated bispecific TAAxCD3-antibodies in order to prevent FcR binding and to allow for a target cell restricted—rather than FcR-mediated activation of T cells (Jung et al. Immunol Today 1988; 9:257-260; Jung et al. Eur J Immunol 1991; 21:2431-2435).

The production of bispecific antibodies meeting this critical prerequisite in industrial quality and quantity remains a formidable challenge. Recently, a recombinant, bispecific single chain (bssc) antibody with CD19xCD3-specificity, termed Blinatumomab, has demonstrated considerable efficiency in the treatment of patients with ALL (Bargou et al. Science 2008, 321:974-977) and has received approval under a break through designation by the FDA. Notably, the drug is applied as continuous 24 hr infusion over several weeks due to its low serum half-life and rather high toxicity: safely applicable doses are approx. 30 µg per patient and day which is 10.000 times lower than those used for treatment with established monospecific antitumor antibodies (Adams and Weiner. Nat Biotechnol 2005, 23:1147-57). The resulting serum concentrations of the drug are below 1 ng/ml (Topp et al. J Clin Oncol 2011; 29:2493-2498). This severe dose limitation, also observed in earlier clinical trials with different bispecific antibodies (Kroesen et al. Br J Cancer 1994; 70:652-661; Tibben et al. Int J Cancer 1996; 66:477-483), is due to off-target T cell activation resulting in systemic cytokine release. Obviously, this phenomenon prevents an optimal therapeutic activity of bispecific antibodies stimulating the TCR/CD3 complex.

In principle, dose limiting off-target T cell activation and the resulting toxicity problem may be caused by the problems P1 and P2 discussed in more detail in the following; low serum half-life is discussed as problem P3:

(P1) The TAA targeted by the bispecific antibody is not entirely tumor specific resulting in antibody mediated T cell activation due to binding to normal, TAA expressing cells. In a strict sense this is no off target activation, since it is induced by antigen expressing target cells albeit the "wrong ones", that is, normal rather than malignant cells. Blinatumomab, the bispecific CD19xCD3-antibody mentioned above, certainly faces this problem since its target antigen CD19 is expressed on normal B lymphocytes. Obviously, the specificity of the targeting antigen for malignant tissue is critical to prevent off-target T cell activation of this kind. PSMA is a particularly suitable antigen in this respect since extensive immunohistologic evaluation has revealed that the expression of this antigen on normal tissue is restricted to prostatic epithelium, mammary gland and proximal tubules of the kidney [human protein atlas, http://www.proteinatlas.org]. On malignant tissue the antigen is abundantly expressed on prostate carcinoma cells and on a variety of other solid tumors, such as colon-, mammary- and pancreatic carcinoma and glioblastoma (Chang et al. Cancer Res 1999, 59:3192; Ross et al. Cancer Met Rev 2005, 24:521). On these latter tumors, however PSMA expression is strictly restricted to the vasculature and spares the tumor cells themselves. Curiously, in prostate carcinoma, the only tumor so far with expression on the tumor cells, the vasculature lacks PSMA expression in most cases (Chang et al. 1999) so that the optimal situation, that is expression on the vasculature as well as on the tumor cells themselves, is rarely present (P1.1).

Apart from its specificity, another property of the targeting antibody may be critical for its therapeutic activity: the antibody may cause an antigen shift either by "shedding" or uptake of the antigen into the target cell. Antigen uptake is desirable in the case of an immunotoxin, which is a construct comprising an antibody and a toxin that usually requires uptake into the cell to exert its activity. However, if antibodies are used to recruit immunologic effector cells, antigen shift by whatever mechanism may hamper the activity of the antibodies. In fact, it has been demonstrated that therapeutic CD20 antibodies induce antigen shift in different lymphoma cells to a variable degree and that this phenomenon is, at least in part, responsible for the variable therapeutic effects of these antibodies (Glennie et al. Mol Immunol. 2007; 44:3823). In any case, in the context of T cell activating bispecific antibodies, it appears desirable to select for targeting antibodies that induce minimal antigen shift (P1.2).

(P2) T cell activation is not—as it should be—target cell restricted, that is, even a monovalent CD3 effector binding site within a bispecific antibody construct is capable of inducing some T cell activation in the absence of target cells to which the antibody binds with its targeting moiety. This represents off-target activation in a strict sense, since cells carrying a target antigen are not required to induce the phenomenon. We have noticed that this phenomenon varies considerably if different CD3 antibodies in different formats are used and if certain stimulating bystander cells (SBCs), such as lymphoma cells (SKW6.4) or endothelial cells (HUVECs) are added that provide co-stimuli for T cell activation. Thus, one should select a CD3 moiety inducing minimal "off-target" T cell activation for the construction of bispecific antibodies (P2.1).

In addition to T cell activation induced by genuinely monomeric CD3 stimulation, a recent paper suggests an alternative mechanism for off-target activation involving the targeting part of a bispecific antibody; if this part consists of a single chain fragment that induces clustering of the effector part of the bispecific antibody on the T cell surface, tonic signaling may be induced resulting in T cell exhaustion (Long et al. Nat Med 2015; 6:581), that is barely detectable by conventional, short term in vitro assays but severely affects in vivo efficiency. These observations have been made using T cells transfected with a chimeric antigen receptor (CAR T cells). Chimeric T cell receptors comprise single chain antibodies as targeting moieties. It is highly likely that the results of Long et al. (2015) likewise apply to bispecific antibodies with such a targeting part, since these reagents, once bound to a T cell, are functionally equivalent to a T cell transfected with the corresponding CAR. It is well known in the field that most single chain antibodies have the tendency to form multimers and aggregates (Worn et al. J Mol Biol 2001, 305:989-1010), and thus it is not surprising that all but one of the CARs tested by Long et al. (2015) showed the phenomenon of clustering and tonic CD3 signaling albeit to a variable degree (Long et al. 2015). The problem outlined here (P.2.2) calls for a bispecific format that prevents multimerization of- and clustering by the targeting part.

P3 Most bispecific formats suffer from a very low serum half-life (1-3 hrs) due to reduced molecular weight and lack of CH3 domains. Thus the prototypical Blinatumomab antibody is applied by continuous 24 hr i.v. infusion over several weeks. The use of whole IgG-based formats with increased serum half-life, such as the IgGsc depicted in FIG. 1B, has been considered unsuitable because the possibly increased off-target activation induced by the bivalent C-terminal CD3 binding moiety.

Based on the above, there is a need in the art for improved antibody molecules that addresses at least one of the problems outlined above.

SUMMARY OF THE INVENTION

The present invention relates to an antibody molecule or an antigen-binding fragment thereof, capable of binding to human prostate specific membrane antigen (PSMA), comprising: (i) a heavy chain variable domain comprising the CDRH1 region set forth in SEQ ID NO: 03 (GFTFSDFYMY), the CDRH2 region set forth in SEQ ID NO: 04 (TISDGGGYTSYPDSVKG), and the CDRH3 region set forth in SEQ ID NO: 05 (GLWLRDALDY) or comprising a CDRH1, CDRH2 or CDRH3 sequence having at least 75% sequence identity or at least 80% sequence identity with SEQ ID NO: 03, SEQ ID NO: 04, or SEQ ID NO: 05; and (ii) a light chain variable domain comprising the CDRL1 region set forth in SEQ ID NO: 06 (SASSSISS-NYLH), the CDRL2 region set forth in SEQ ID NO: 07 (RTSNLAS), and the CDRL3 region set forth in SEQ ID NO: 08 (QQGSYIPFT) or comprising a CDRL1, CDRL2 or CDRL3 sequence having at least 75% sequence identity or at least 80% sequence identity with SEQ ID NO: 06, SEQ ID NO: 07, or SEQ ID NO: 08.

The present invention also relates to an antibody molecule or an antigen-binding fragment thereof, capable of binding to human PSMA that is able to compete with the binding of an antibody molecule of the invention or antigen-binding fragment thereof to human PSMA.

The present invention further relates a bispecific antibody molecule comprising (i) a variable region comprising a heavy chain variable domain and a light chain variable domain of an PMSA binding antibody molecule of the invention, wherein said variable region comprises a first binding site capable of binding to human prostate specific membrane antigen (PSMA); and (ii) a heavy chain variable region and a light chain variable region of an antibody molecule comprising a second binding site.

The present invention further relates to a pharmaceutical composition comprising an antibody molecule of the invention or an antigen-binding fragment thereof.

The present invention further relates to an antibody molecule of the invention or an antigen-binding fragment thereof for use in the diagnosis or treatment of a disease.

The present invention further relates to an in vitro method of diagnosing a disease comprising contacting a sample obtained from a subject with an antibody molecule of the invention or an antigen-binding fragment thereof.

The present invention further relates to a nucleic acid molecule encoding an antibody molecule of the invention or an antigen-binding fragment thereof, a vector comprising said nucleic acid molecule, and a host cell comprising said nucleic acid molecule or said vector.

The present invention further relates to a method of producing an antibody molecule of the invention or an antigen-binding fragment thereof, comprising expressing a nucleic acid encoding the antibody molecule under conditions allowing expression of the nucleic acid.

BRIEF DESCRIPTION OF THE DRAWINGS

The invention will be better understood with reference to the detailed description when considered in conjunction with the non-limiting examples and the accompanying drawings, in which:

In FIG. 3A off-target T cell activation in the absence of target cells is shown while FIG. 3B depicts, in comparison, on-target T cell activation with PSMAxCD3 antibodies in the Fabsc-format and contain the CD3 antibodies UCHT1 (NPCU) and OKT3 (NPCO), respectively. In FIG. 3C lysis of PSMA expressing target cells by activated T cells is demonstrated by an Xelligence cytotoxicity assay.

In FIG. 4A and FIG. 4B antibodies with FLT3xCD3-specificity are compared (Fabsc- vs. bssc-format) while in FIGS. 4C-4F those with PSMAxCD3-specificity are compared (Fabsc- vs. IgGsc-format). Gel filtration was performed on Superdex S200 columns.

FIGS. 5A-5C depict the binding of the prior art PSMA-antibody J591 and the antibody of the invention 10B3 to PSMA-expressing cells. Binding (FIG. 5A), lack of binding competition (FIG. 5B) and shift of the PSMA antigen upon antibody binding (FIG. 5C) was assessed by flow cytometry using PSMA-transfected Sp2/0 cells. In FIG. 5B it is demonstrated that chimeric (ch) J591, specifically detected by a goat anti human secondary antibody, was out-competed by murine (mu) J591 but not murine 10B3.

In FIG. 6A and FIG. 6B a prostate carcinoma sample was stained with both antibodies in parallel and a polymer system from Zytomed, Berlin, Germany (POLHRP-100) while in FIG. 6C and FIG. 6D a squamous cell carcinoma sample was stained with the two antibodies again in parallel using the polymer system from Zytomed. Arrows indicate tumor stroma (Tu) and blood vessels (Ve). Representative results from 9 of 10 prostate cancer samples and 7 of 10 squamous cell carcinoma samples are shown. On a variety of different normal human tissues (obtained from BioCat, Heidelberg, Germany, T6234701-2) the staining pattern of the two antibodies was identical with the exception of a faint reactivity of 10B3 with epithelial cells in the skin.

FIG. 9 depicts cytolytic activity of the different PSMA antibodies. PSMA expressing 22RV1 prostate carcinoma cells were incubated with PBMCs and the indicated bispecific PSMAxCD3 antibodies at a PBMC:target ratio of 5:1. The viability of the adherent target cells was assessed using an Xelligence system. Representative results of one out of four different experiments with PBMCs of different healthy volunteers are shown.

FIGS. 10A-10D show the amino acid sequence of heavy and light chain variable regions of murine and humanized 10B3 antibody. FIG. 10A shows the amino acid sequence of the heavy chain variable region of the murine 10B3 antibody (SEQ ID NO: 01). CDR sequences are underlined. FIG. 10B shows the amino acid sequence of the light chain variable region of the murine 10B3 antibody (SEQ ID NO: 02). CDR sequences are underlined. FIG. 10C shows the amino acid sequence of the heavy chain variable region of humanized 10B3 antibody in which the CDR loops (CDRH1, CDRH2, and CHDR3) of the heavy chain of the murine antibody 10B3 are grafted onto the variable domain of the of the heavy chain germ line sequence IGHV3-11*06 (SEQ ID NO: 09). CDR sequences are underlined. In addition, the serine residue that is present at position 49 of the heavy chain germ line sequence IGHV3-11*06 is back-mutated in the variable domain of SEQ ID NO:9 to an alanine that is present in the murine antibody 10B3. This alanine residue at position 49 is highlighted in bold and italics in FIG. 10C). FIG. 10D shows the amino acid sequence of the light chain variable region of humanized 10B3 antibody in which the CDR loops (CDRL1, CDRL2, CDRL3 of the light chain of the antibody 10B3 are grafted onto the variable domain of the human κ light sequence IGKV3-20*02 (SEQ ID NO: 10). CDR sequences are underlined. In addition, the phenylalanine present at sequence position 72 in the variable domain of the human light chain sequence of IGKV3-20*02 is back-mutated in the variable domain of SEQ ID NO:10 to the tyrosine residue that is present at this sequence position in the murine antibody 10B3. This tyrosine residue at position 72 is highlighted in bold and italics in FIG. 10D.

FIG. 11 shows the amino acid sequence of the heavy chain of the PSMA (humanized h10B3) X CD3 (humanized hUCHT1) bispecific IgGsc format antibody molecule (SEQ ID NO: 11). The heavy chain comprises the humanized heavy chain (HC) variable region of 10B3, an IgG1 CH1 domain, an IgG1 hinge region, a modified IgG1 CH2 domain, an IgG1 CH3 domain, and a humanized CD3 (UCHT1) single chain Fv fragment.

FIG. 12 shows the amino acid sequence of the heavy chain of the PSMA (humanized h10B3) X CD3 (murine OKT3) bispecific Fabsc format antibody molecule (SEQ ID NO: 12). The heavy chain comprises a humanized HC variable region of 10B3, an IgG1 CH1 domain, an IgG1 hinge region, a modified IgG1 CH2 domain, the beginning of an IgG1 CH3 domain, and a murine CD3 (OKT3) single chain Fv fragment.

FIG. 13 shows the amino acid sequence of the kappa light chain of the PSMA (humanized h10B3) antibody (SEQ ID NO: 13). This light chain completes the heavy chain constructs of SEQ ID NO: 11 and SEQ ID NO: 12 to form an h10B3xUCHT1 IgGsc- and a h10B3xOKT3 Fabsc-molecule, respectively (see FIG. 1).

FIGS. 14A-14B show the amino acid sequence of the variable domains of the antibody J519, with FIG. 14A showing the amino acid sequence of the variable domain of the heavy chain (SEQ ID NO: 15) and FIG. 14B showing the amino acid sequence of the variable domain of the light chain (SEQ ID NO: 16) of the antibody J519.

FIGS. 15A-15F show the therapeutic effect of the bispecific antibody of the invention in vitro. PSMA (humanized h1B3) X CD3 (humanized hUCHT1) bispecific IgGsc format antibody molecule of the invention and control bispecific antibody (NG2xCD3) was incubated in the presence of PBMC with or without tumor cells.

FIGS. 16A-16D show the in vivo anti-tumor activity of the PSMA (humanized h1B3) X CD3 (humanized hUCHT1) bispecific IgGsc format antibody molecule of the invention in a mouse model.

DETAILED DESCRIPTION

Figure 1A:
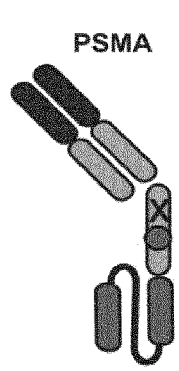
FIGS. 1A-1C depict various formats of bispecific antibody molecules that have been used in the present invention. Depicted are bispecific PSMAxCD3 antibodies in the Fabsc-format (FIG. 1A) and IgGsc-format (FIG. 1B). In both formats binding of the CH2 domain to Fc-receptors is prevented by defined amino acid modifications. Also depicted is the bssc (bispecific single chain Fv) format (FIG. 1C).

The present invention relates to an antibody, an antibody molecule or an antigen-binding fragment thereof that is capable of binding to human prostate specific membrane antigen (PSMA). The antibody, antibody molecule or antigen-binding fragment thereof comprises (i) a heavy chain variable domain comprising the CDRH1 region set forth in SEQ ID NO: 3 (having the amino acid sequence GFTFSDFYMY), the CDRH2 region set forth in SEQ ID NO: 4 (having the amino acid sequence TISDGGGYT-SYPDSVKG), and the CDRH3 region set forth in SEQ ID NO: 5 (having the amino acid sequence GLWLRDALDY) or comprising a CDRH1, CDRH2 or CDRH3 sequence having at least 75% sequence identity or at least 80% sequence identity with SEQ ID NO: 3, SEQ ID NO:4, or SEQ ID NO: 5. It further comprises (iii) a light chain variable domain comprising the CDRL1 region set forth in SEQ ID NO: 6 (having the amino acid sequence SASSSISS-NYLH), the CDRL2 region set forth in SEQ ID NO: 7 (having the amino acid sequence RTSNLAS), and the CDRL3 region set forth in SEQ ID NO: 8 (having the amino acid sequence QQGSYIPFT) or comprising a CDRL1, CDRL2 or CDRL3 sequence having 75% sequence identity or 80% sequence identity with SEQ ID NO: 6, SEQ ID NO:7, or SEQ ID NO: 8. Envisioned by the invention is an antibody molecule comprising the CDRH1 region set forth in SEQ ID NO: 3, the CDRH2 region set forth in SEQ ID NO: 4, the CDRH3 region set forth in SEQ ID NO: 5, the CDRL1 region set forth in SEQ ID NO: 6, the VLCDL2 region set forth in SEQ ID NO: 7, and the VLCDL3 region set forth in SEQ ID NO: 8. In this context, it is noted that the antibody molecule of the present invention or antigen binding fragment thereof preferably does not compete with the binding of the antibody J591 (Liu et al., Cancer Res 1997; 57: 3629-34, which is the most highly developed antibody clinically see the review of Akhtar et al "Prostate-Specific Membrane Antigen-Based Therapeutics", Advances in Urology Volume 2012 (2012), Article ID 973820) to human PSMA. In addition, an antibody molecule of the present invention or antigen binding fragment thereof may have a reduced induction of antigen shift when binding to PSMA compared to J591. It may also exert a unique reactivity with squamous carcinoma cells of different origin.

The present invention further relates to an antibody, an antibody molecule or antigen-binding fragment thereof comprises a heavy chain variable region that comprises the amino acid sequence having a sequence identity of at least 90% to the amino acid sequence set forth in SEQ ID NO: 01 or 09. Also encompassed by the invention is an antibody, an antibody molecule or an antigen-binding fragment thereof, comprising a light chain variable region, wherein the light chain variable region comprises the amino acid sequence having a sequence identity of at least 90% to the amino acid sequence set forth in SEQ ID NO: 02 or SEQ ID NO: 10. Particularly preferred is an antibody, an antibody molecule or antigen-binding fragment thereof comprising a heavy chain variable domain and a light chain variable domain of the murine anti-PSMA antibody 10B3 (m10B3) as set forth in SEQ ID NO: 01 and 02, respectively. Also preferred is an antibody, an antibody molecule or antigen-binding fragment thereof comprising a heavy chain variable domain and a light chain variable domain of the humanized anti-PSMA antibody 10B3 (h10B3) as set forth in SEQ ID NO: 09 and 10, respectively.

PSMA is a particularly attractive antigen for antibody mediated targeting, and several antibodies directed to the extracellular portion of this protein have been developed. The most advanced reagent, J591 (Liu et al., Cancer Res 1997; 57: 3629-34), is currently evaluated in clinical trials, either radiolabeled or coupled to the toxin DM1, a derivative of maytansin, a tubulin inhibiting compound (Ross J S, et al. Cancer Met Rev 2005; 24:521; Akhtar et al, 2012, supra). The PSMA antibody of the invention has an identical reaction pattern with normal human tissue. The PSMA antibody of the present invention however differs from the antibody J591 in its reaction with squamous carcinoma cells of different origin. It has been surprisingly found here that in these tumors, as well as in cancer of the prostate both, the tumor cells themselves and the vasculature within and around the tumor are stained by an PMSA antibody such as the antibody 10B3 that contains the CDR sequences of the heavy and light chain variable domains as depicted in SEQ ID NO:3 to SEQ ID NO: 8 (cf. FIGS. 6A-6D). Squamous carcinomas make up the majority of cancers arising in the ear nose and throat compartment, the esophagus and the cervix uteri as well as 20-30% of lung tumors, and PSMA expression on such tumors has not been described before. Thus, the favorable reactivity of the antibody of the present invention with these cancers offers extended and improved diagnostic and treatment options.

The PSMA antibody J591 and the antibody of the present invention differ in another important respect: In general, many antibodies induce a profound antigen shift upon binding to a target cell, a desired property e.g. for the construction of immunotoxins that require uptake into the cells to exert biological activity. The benchmark PSMA antibody J591, for example, is used for such a purpose (Ross et al. 2005, supra). If, however, recruitment of immunological effector cells is desired, a stable expression of the antigen is preferable rather than its rapid uptake into the cell. FIGS. 5A-5C demonstrate that binding of an antibody of the present invention to PSMA transfected Sp2/0 cells is comparable to that of J591 (FIG. 5A) and that the two antibodies do not cross-compete each other, indicating that they bind to different epitopes of the PSMA molecule (FIG. 5B). Most importantly, the antibody of the present invention induces a reduced antigen shift if compared to J591 (FIG. 5C). In this context, it is however noted that the epitope on PMSA to which the antibody 10B3 binds is not yet known. It is also noted in this respect that the epitope to which the antibody 10B3 binds on squamous carcinoma cells may not necessarily be the same as the epitope on PMSA, in particular as PMSA expression has not yet been reported on squamous carcinoma cells. The epitope or epitopes to which an antibody molecule of the invention binds on squamous carcinoma cells may thus be only related to the epitope on PMSA with respect to their amino acid sequence or their confirmation. However, the nature of the respective epitope on PMSA or squamous carcinoma cells is not relevant in the present invention as long as an antibody molecule of the present invention binds to cells expressing PMSA or to squamous carcinoma cells as described here. It is also noted here that the binding of an antibody molecule of the present invention to a cell does not necessarily have to trigger a physiological response. Rather, it is sufficient that the antibody of the invention binds to (the epitope present on) a given cell. If, for example, conjugated to a cell-toxic agent such a toxin or a radioactive ligand, the antibody serves, for therapeutic purposes, as delivery or targeting moiety that brings the cell-toxic agent to the cell on which the cell toxic agent should exercise its cell toxic (cell-killing) activity. Likewise, when used for diagnostic purposes, an antibody of the invention may be conjugated to an imaging moiety that provides a detectable signal that can be used for detection of the cell to which the antibody has bound.

The present invention also provides a humanized version of 10B3, which has been humanized by CDR grafting, meaning the CDR regions of the murine antibody 10B3 are inserted into the framework region of a heavy chain and a light chain of a human antibody. In principle any variable human light chain and/or variable heavy chain can serve as scaffold for the CDR grafting. In one illustrative example of a humanized antibody of the invention, the CDR regions of the light chain of the antibody 10B3 (that means the CDR loops of SEQ ID NO: 6 to SEQ ID NO: 8) can be inserted into (the variable domain) of the human κ light sequence IGKV3-20*02 that is deposited in the IMGT/LIGM-database under accession number L37729, see also Ichiyoshi Y., Zhou M., Casali P. A human anti-insulin IgG autoantibody apparently arises through clonal selection from an insulin-specific 'germ-line' natural antibody template. Analysis by V gene segment reassortment and site-directed mutagenesis' *J. Immunol.* 154(1):226-238 (1995). In another illustrative example of a humanized antibody of the invention, the CDR regions of the heavy chain of the antibody 10B3 (that means the CDR loops of SEQ ID NO: 3 to SEQ ID NO: 5) can be included into the (variable domains) of the heavy chain sequence IGHV3-11*06 which is deposited in the IMGT/LIGM-database under accession number AF064919 (See also Watson C. T., et al. Complete haplotype sequence of the human immunoglobulin heavy-chain variable, diversity, and joining genes and characterization of allelic and copy-number variation. *Am. J. Hum. Genet.* 92(4):530-546 (2013). In a further illustrative embodiment of a humanized antibody as described herein, the CDR loops of the heavy chain of the antibody 10B3 are grafted onto the variable domain of the heavy chain germ line sequence IGHV3-11*06 and the CDR loops of the light chain of the antibody 10B3 are grafted onto the variable domain of the human κ light sequence IGKV3-20*02. In order to maintain the binding properties of the parental murine antibody 10B3, it may be possible that residues of human framework are mutated back to the amino acid residue that is present at a particular sequence position of the murine antibody 10B3. In an illustrative example of such a humanized antibody, in the variable domain of the heavy chain of the human germline sequence of IGHV3-11*06 the serine at position 49 was back-mutated to an alanine that is present in the murine antibody 10B3 (see also FIG. 10C in which the alanine residue at position 49 is highlighted in bold and italics) while in the variable domain of the light chain sequence of IGKV3-20*02 the phenylalanine at sequence position 72 of the human germline sequence was back-mutated to a tyrosine residue that is present at this sequence position in the murine antibody 10B3 (see also FIG. 10D in which the tyrosine residue at position 72 is highlighted in bold and italics). Such a humanized antibody, incorporated into a bispecific Fabsc-antibody, binds with the same avidity to the PSMA expressing cell line than the mouse parental antibody (cf. FIG. 7).

The term "antibody" generally refers to a proteinaceous binding molecule that is based on an immunoglobulin. Typical examples of such an antibody are derivatives or functional fragments of an immunoglobulin which retain the binding specificity. Techniques for the production of antibodies and antibody fragments are well known in the art. The term "antibody" also includes immunoglobulins (Ig's) of different classes (i.e. IgA, IgG, IgM, IgD and IgE) and subclasses (such as IgG1, IgG2 etc.). As also mentioned above, illustrative examples of an antibody derivative or molecule include Fab fragments, F(ab')$_2$, Fv fragments, single-chain Fv fragments (scFv), diabodies or domain antibodies (Holt L J et al., Trends Biotechnol. 21(11), 2003, 484-490). The definition of the term "antibody" thus also includes embodiments such as chimeric, single chain and humanized antibodies.

An "antibody molecule" as used herein may carry one or more domains that have a sequence with at least about 60%, at least about 70%, at least about 75%, at least about 80%, at least about 85%, at least about 90%, at least about 92%, at least about 95%, at least about 96%, at least about 97%, at least about 98% or at least about 99% sequence identity with a corresponding naturally occurring domain of an immunoglobulin M, an immunoglobulin G, an immunoglobulin A, an immunoglobulin D or an immunoglobulin E. It is noted in this regard, the term "about" or "approximately" as used herein means within a deviation of 20%, such as within a deviation of 10% or within 5% of a given value or range.

"Percent (%) sequence identity" as used in the present invention means the percentage of pair-wise identical residues—following homology alignment of a sequence of a polypeptide of the present invention with a sequence in question—with respect to the number of residues in the longer of these two sequences. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared. The same is true for nucleotide sequences disclosed herein. In this context, the sequence identity of at least 75% or at least 80% as described herein is illustrated with respect for the CDR sequence of an antibody of the invention. Referring first to CDR H1, an antibody of the invention has a CDRH1 sequence GFTFSDFYMY (SEQ ID NO: 3) or an amino acid sequence having 80% sequence identity with this sequence. Since this CDRH1 sequence has a length of 10 amino acid, 2 of these 10 residues can be replaced to have a sequence identity of 80% to SEQ ID NO:3. It is for example possible that the threonine residue at position 3 of CDR H1 is replaced by a serine (making a conservative substitution) and the serine residue at position 5 of CDRH1 is replaced by a threonine residue (meaning also by a conservative substitution). Thus, the resulting sequence GFSFTDFYMY (SEQ ID NO: 14) of CDRH1 which carries these two conservative amino acid exchanges relative to SEQ ID NO: 3 has a sequence identity of 80% to the sequence of SEQ ID NO: 3, while a CDR H1 sequence in which only one of these two conservative substitutions are made has a sequence identity of 90% with the sequence of SEQ ID NO: 3. Similarly, the CDRH2 sequence set forth in SEQ ID NO: 04 (TISDGG-GYTSYPDSVKG) contains 17 amino acid residues, a sequence identity of 80% allows up to 3 mutations relative to the sequence of SEQ ID NO: 04 (since 20% theoretically corresponds to 3.4 different amino acids). For example, the first threonine residue of SEQ ID NO: 4 may be replaced by a serine. Similarly, the CDRH3 region set forth in SEQ ID NO: 05 (GLWLRDALDY) has a length of 10 amino acid residues. Thus, a CDRH3 sequence that has 80% or 90% sequence identity to SEQ ID NO: 05 (GLWLRDALDY) can comprise two amino acid replacements, for example, conservative substitutions, compared to SEQ ID NO: 5. The CDRL1 region set forth in SEQ ID NO: 06 (SASSSISS-NYLH) comprises 12 amino acid residues. Thus, a CDRL1 sequence that carries one or two amino acid substitutions compared to the amino acid sequence of SEQ ID NO: 06 has a sequence identity of more than 80% to the sequence of SEQ ID NO: 06. The CDRL2 region set forth in SEQ ID NO: 07 (RTSNLAS) has a length of 7 amino acid residues. Thus, a CDRL2 sequence that contains one amino acid substitution compared to the CDRL2 sequence of SEQ ID NO: 7 has a sequence identity of 84% to the SEQ ID NO: 07. Finally, the CDRL3 region set forth in SEQ ID NO: 08

(QQGSYIPFT) has a length of 9 amino acid residues. Accordingly, a CDRL3 sequence that comprises one substituted amino acid compared to the sequence of SEQ NO: 08 has a sequence identity of 89% to SEQ ID NO: 8 and a CDL3 sequence that comprises two amino acid substitutions compared to SEQ ID NO: 08 has a sequence identity of 78% to the sequence of SEQ ID NO: 08. It is noted here that from the above explanation and the sequences of the CDR regions described herein, the person skilled in the art will understand that any sequences that has at least 80% sequence identity to the sequence of any of the CDRH1, CDRH2, CDHL3, CDRL1, CDRL2 and CDRL3 described herein (SEQ ID NO: 03 to SEQ ID NO: 08) and that is able to bind to bind PMSA and preferably also to squamous carcinoma cells as described herein is encompassed in the present invention. While the CDR sequence that has at least 75%, at least 80%, at least 85%, or at least 90% sequence identity to the respective CDR sequence of any of SEQ ID NO: 03 to SEQ ID NO: 08 comprises preferably one or more conservative mutations, it is also possible that the deviation to the sequence of any of the six "parental" CDR regions (SEQ ID NO: 3 to SEQ ID NO: 8) of the antibody of the invention and thus a sequence identity of 75% or more is due to the presence of no-conservative mutations in the CDR regions as long as the antibody retains the ability to bind PMSA and preferably also to squamous carcinoma cells.

An "immunoglobulin" when used herein, is typically a tetrameric glycosylated protein composed of two light (L) chains of approximately 25 kDa each and two heavy (H) chains of approximately 50 kDa each. Two types of light chain, termed lambda and kappa, may be found in immunoglobulins. Depending on the amino acid sequence of the constant domain of heavy chains, immunoglobulins can be assigned to five major classes: A, D, E, G, and M, and several of these may be further divided into subclasses (isotypes), e.g., IgG1, IgG2, IgG3, IgG4, IgA1, and IgA2. An IgM immunoglobulin consists of 5 of the basic heterotetramer unit along with an additional polypeptide called a J chain, and contains 10 antigen binding sites, while IgA immunoglobulins contain from 2-5 of the basic 4-chain units which can polymerize to form polyvalent assemblages in combination with the J chain. In the case of IgGs, the 4-chain unit is generally about 150,000 Daltons.

In the IgG class of immunoglobulins, there are several immunoglobulin domains in the heavy chain. By "immunoglobulin (Ig) domain" herein is meant a region of an immunoglobulin having a distinct tertiary structure. In the context of IgG antibodies, the IgG isotypes each have three CH regions: "CH1" refers to positions 118-220, "CH2" refers to positions 237-340, and "CH3" refers to positions 341-447 according to the EU index as in Kabat et al. By "hinge" or "hinge region" or "antibody hinge region" or "immunoglobulin hinge region" or "H" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the hinge is herein defined to include positions 221 (D221 in IgG1) to 236 (G236 in IgG1), wherein the numbering is according to the EU index as in Kabat et al. The constant heavy chain, as defined herein, refers to the N-terminus of the CH1 domain to the C-terminus of the CH3 domain, thus comprising positions 118-447, wherein numbering is according to the EU index.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable regions", "HVR," or "HV," or "complementarity determining regions" (CDRs). The more conserved (i.e., non-hypervariable) portions of the variable domains are called the "framework" regions (FR). The variable domains of naturally occurring heavy and light chains each include four FR regions, largely adopting a 3-sheet configuration, connected by three hypervariable regions, which form loops connecting, and in some cases forming part of, the 3-sheet structure. The hypervariable regions in each chain are held together in close proximity by the FR and, with the hypervariable regions from the other chain, contribute to the formation of the antigen-binding site (see Kabat et al., see below). Generally, naturally occurring immunoglobulins include six CDRs (see below); three in the VH (H1, H2, H3), and three in the VL (L1, L2, L3). In naturally occurring immunoglobulins, H3 and L3 display the most extensive diversity of the six CDRs, and H3 in particular is believed to play a unique role in conferring fine specificity to immunoglobulins. The constant domains are not directly involved in antigen binding, but exhibit various effector functions, such as, for example, antibody-dependent, cell-mediated cytotoxicity and complement activation.

The terms "$V_H$" (also referred to as VH) and "$V_L$" (also referred to as VL) are used herein to refer to the heavy chain variable domain and light chain variable domain respectively of an immunoglobulin. An immunoglobulin light or heavy chain variable region consists of a "framework" region interrupted by three hypervariable regions. Thus, the term "hypervariable region" refers to the amino acid residues of an antibody which are responsible for antigen binding. The hypervariable region includes amino acid residues from a "Complementarity Determining Region" or "CDR". There are three heavy chains and three light chain CDRs (or CDR regions) in the variable portion of an immunoglobulin. Thus, "CDRs" as used herein refers to all three heavy chain CDRs (CDRH1, CDRH2 and CDRH3), or all three light chain CDRs (CDRL1, CDRL2 and CDRL3) or both all heavy and all light chain CDRs, if appropriate. Three CDRs make up the binding character of a light chain variable region and three make up the binding character of a heavy chain variable region. CDRs determine the antigen specificity of an immunoglobulin molecule and are separated by amino acid sequences that include scaffolding or framework regions. The exact definitional CDR boundaries and lengths are subject to different classification and numbering systems. The structure and protein folding of the antibody may mean that other residues are considered part of the antigen binding region and would be understood to be so by a skilled person. CDRs provide the majority of contact residues for the binding of the immunoglobulin to the antigen or epitope.

CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988. One of skill in the art will recognize that each subunit structure, e.g., a CH, VH, CL, VL, CDR, FR structure, includes active fragments, e.g., the portion of the VH, VL, or CDR subunit binds to the antigen, i.e., the antigen-binding fragment, or, e.g., the portion of the CH subunit that binds to and/or activates, e.g., an Fc receptor and/or complement. The CDRs typically refer to the Kabat CDRs, as described in Sequences of Proteins of immunological Interest, US Department of Health and Human Services (1991), eds. Kabat et al. Another standard for characterizing the antigen binding site is to refer to the hypervariable loops as described by Chothia. See, e.g., Chothia, et al. (1992; J. MoI. Biol. 227:799-817; and Tomlinson et al. (1995) EMBO J. 14:4628-4638. Still another standard is the AbM definition used by Oxford Molecular's AbM antibody modelling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). Embodiments described with respect to Kabat CDRs can alternatively be implemented using similar described relationships with respect to Chothia hypervariable loops or to the AbM-defined loops.

The corresponding immunoglobulin mu heavy chain, gamma heavy chain, alpha heavy chain, delta heavy chain, epsilon heavy chain, lambda light chain or kappa light chain may be of any species, such as a mammalian species, including a rodent species, an amphibian, e.g. of the subclass Lissamphibia that includes e.g. frogs, toads, salamanders or newts or an invertebrate species. Examples of mammals include, but are not limited to, a rat, a mouse, a rabbit, a guinea pig, a squirrel, a hamster, a hedgehog, a platypus, an American pika, an armadillo, a dog, a lemur, a goat, a pig, a cow, an opossum, a horse, a bat, a woodchuck, an orang-utan, a rhesus monkey, a woolly monkey, a macaque, a chimpanzee, a tamarin (*Saguinus oedipus*), a marmoset or a human.

As mentioned herein an immunoglobulin is typically a glycoprotein that includes at least two heavy (H) chains and two light (L) chains linked by disulfide bonds, or an antigen binding portion thereof. Each heavy chain has a heavy chain variable region (abbreviated herein as $V_H$) and a heavy chain constant region. In some embodiments the heavy chain constant region includes three domains, $C_{H1}$, $C_{H2}$ and $C_{H3}$. Each light chain has a light chain variable region (abbreviated herein as $V_L$) and a light chain constant region. The light chain constant region includes one domain, $C_L$. The $V_H$ and $V_L$ regions can be further subdivided into regions of hypervariability, termed complementarity determining regions (CDR), interspersed with regions that are more conserved, termed framework regions (FR). The CDRs contain most of the residues responsible for specific interactions of the antibody with the antigen. Each $V_H$ and $V_L$ has three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an epitope of an antigen.

"Framework Region" or "FR" residues are those variable domain residues other than the hypervariable region. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

The terms "Fab", "Fab region", "Fab portion" or "Fab fragment" are understood to define a polypeptide that includes a $V_H$, a $C_H1$, a $V_L$, and a $C_L$ immunoglobulin domain. Fab may refer to this region in isolation, or this region in the context of an antibody molecule, as well as a full length immunoglobulin or immunoglobulin fragment. Typically a Fab region contains an entire light chain of an antibody. A Fab region can be taken to define "an arm" of an immunoglobulin molecule. It contains the epitope-binding portion of that Ig. The Fab region of a naturally occurring immunoglobulin can be obtained as a proteolytic fragment by a papain-digestion. A "F(ab')$_2$ portion" is the proteolytic fragment of a pepsin-digested immunoglobulin. A "Fab' portion" is the product resulting from reducing the disulfide bonds of an F(ab')$_2$ portion. As used herein the terms "Fab", "Fab region", "Fab portion" or "Fab fragment" may further include a hinge region that defines the C-terminal end of the antibody arm. This hinge region corresponds to the hinge region found C-terminally of the CH1 domain within a full length immunoglobulin at which the arms of the antibody molecule can be taken to define a Y The term hinge region is used in the art because an immunoglobulin has some flexibility at this region. A "Fab heavy chain" as used herein is understood as that portion or polypeptide of the Fab fragment that comprises a $V_H$ and a $C_H1$, whereas a "Fab light chain" as used herein is understood as that portion or polypeptide of the Fab fragment that comprises a $V_L$, and a $C_L$.

The term "Fc region" or "Fc fragment" is used herein to define a C-terminal region of an immunoglobulin heavy chain, including native-sequence Fc regions and variant Fc regions. The Fc part mediates the effector function of antibodies, e.g. the activation of the complement system and of Fc-receptor bearing immune effector cells, such as NK cells. In human IgG molecules, the Fc region is generated by papain cleavage N-terminal to Cys226. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody molecule, or by recombinantly engineering the nucleic acid encoding a heavy chain of the antibody molecule. Native-sequence Fc regions include mammalian, e.g. human or murine, IgG1, IgG2 (IgG2A, IgG2B), IgG3 and IgG4. The Fc region contains two or three constant domains, depending on the class of the antibody. In embodiments where the immunoglobulin is an IgG the Fc region has a CH2 and a CH3 domain.

The term "single-chain variable fragment" (scFv) is used herein to define an antibody fragment, in which the variable regions of the heavy (VH) and light chains (VL) of a immunoglobulin are fused together, which are connected with a short linker peptide of ten to about 25 amino acids. The linker is usually rich in glycine for flexibility, as well as serine or threonine for solubility, and can either connect the N-terminus of the VH with the C-terminus of the VL, or connect the N-terminus of the VL with the C-terminus of the VH. The scFv fragment retains a specific antigen binding site but lacks constant domains of immunoglobulins.

The term "epitope", also known as the "antigenic determinant", refers to the portion of an antigen to which an antibody or T-cell receptor specifically binds, thereby forming a complex. Thus, the term "epitope" includes any molecule or protein determinant capable of specific binding to an immunoglobulin or T-cell receptor. The binding site(s) (paratope) of an antibody molecule described herein may specifically bind to/interact with conformational or continuous epitopes, which are unique for the target structure. Epitopic determinants usually consist of chemically active surface groupings of molecules such as amino acids or sugar side chains and usually have specific three dimensional structural characteristics, as well as specific charge characteristics. In some embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. With regard to polypeptide antigens a conformational or discontinuous epitope is characterized by the presence of two or more discrete amino acid residues, separated in the primary sequence, but assembling to a consistent structure on the surface of the molecule when the polypeptide folds into the native protein/antigen (SeIa, M., Science (1969) 166, 1365-1374; Laver, W. G, et al. Cell (1990) 61, 553-556). The two or more discrete amino acid residues contributing to the epitope may be present on separate sections of one or more polypeptide chain(s). These residues come together on the surface of the molecule when the polypeptide chain(s) fold(s) into a three-dimensional structure to constitute the epitope. In contrast, a continuous or linear epitope consists of two or more discrete amino acid residues, which are present in a single linear segment of a polypeptide chain.

The term "specific" in this context, or "specifically binding", also used as "directed to", means in accordance with this invention that the antibody or immune receptor fragment is capable of specifically interacting with and/or binding to a specific antigen or ligand or a set of specific antigens or ligands but does not essentially bind to other antigens or ligands. Such binding may be exemplified by the specificity of a "lock-and-key-principle". Antibodies are said to "bind to the same epitope" if the antibodies cross-compete so that only one antibody can bind to the epitope at a given point of time, i.e. one antibody prevents the binding or modulating effect of the other.

Typically, binding is considered specific when the binding affinity is higher than $10^{-6}$ M or $10^{-7}$ M. In particular, binding is considered specific when binding affinity is about $10^{-8}$ to $10^{-11}$ M ($K_D$), or of about $10^{-9}$ to $10^{-11}$ M or even higher. If necessary, nonspecific binding of a binding site can be reduced without substantially affecting specific binding by varying the binding conditions.

The term "isolated antibody molecule" as used herein refers to an antibody molecule that has been identified and separated and/or recovered from a component of its natural environment. Contaminant components of its natural environment are matter that would interfere with diagnostic or therapeutic uses for the antibody, and may include enzymes, hormones, and other proteinaceous or nonproteinaceous solutes. In some embodiments the antibody molecule is purified to greater than 95% by weight of antibody as determined by the Lowry method, such as more than 99% by weight. In some embodiments the antibody is purified to homogeneity as judged by SDS-PAGE under reducing or nonreducing conditions using Coomassie blue or, preferably, silver stain. An isolated antibody molecule may in some embodiments be present within recombinant cells with one or more component(s) of the antibody's natural environment not being present. Typically an isolated antibody is prepared by at least one purification step.

A (recombinant) antibody molecule of the invention that binds to PMSA and/or squamous cancer cells as described herein may be used in any suitable recombinant antibody format, for example as an Fv fragment, a scFv, a univalent antibody lacking a hinge region, a minibody, a Fab fragment, a Fab' fragment, a F(ab')$_2$ fragment. A recombinant antibody molecule of the invention may also comprise constant domains (regions) such a human IgG constant region, a CH1 domain (as Fab fragments do) and/or an entire Fc region. Alternatively, an antibody molecule of the invention may also be a full length (whole) antibody.

There are a number of possible mechanisms by which antibodies mediate cellular effects, including anti-proliferation via blockage of needed growth pathways, intracellular signaling leading to apoptosis, enhanced down regulation and/or turnover of receptors, complement-dependent cytotoxicity (CDC), antibody-dependent cell-mediated cytotoxicity (ADCC), antibody-dependent cell-mediated phagocytosis (ADCP) and promotion of an adaptive immune response (Cragg et al, 1999, Curr Opin Immunol 11 541-547, Glennie et al, 2000, Immunol Today 21 403-410). Antibody efficacy may be due to a combination of these mechanisms, and their relative importance in clinical therapy for oncology appears to be cancer dependent.

The importance of FcγR-mediated effector functions for the activity of some antibodies has been demonstrated in mice (Clynes et al, 1998, Proc Natl Acad Sci USA 95 652-656, Clynes et al, 2000, Nat Med 6 443-446), and from observed correlations between clinical efficacy in humans and their allotype of high (V158) or low (F158) affinity polymorphic forms of FcγRIIIa (Cartron et al, 2002, Blood 99 754-758, Weng & Levy, 2003, Journal of Clinical Oncology, 21 3940-3947). Together these data suggest that an antibody that is optimized for binding to certain FcγRs may better mediate effector functions, and thereby destroy target cells more effectively in patients. Thus a promising means for enhancing the anti-tumor potency of antibodies is via enhancement of their ability to mediate cytotoxic effector functions such as ADCC, ADCP, and CDC Additionally, antibodies can mediate anti-tumor mechanism via growth inhibitory or apoptotic signaling that may occur when an antibody binds to its target on tumor cells. Such signaling may be potentiated when antibodies are presented to tumor cells bound to immune cells via FcγR. Therefore increased affinity of antibodies to FcγRs may result in enhanced antiproliferative effects.

Some success has been achieved at modifying antibodies with selectively enhanced binding to FcγRs to provide enhanced effector function. Antibody engineering for optimized effector function has been achieved using amino acid modifications (see for example US patent application US 2004-0132101 or US patent application 2006-0024298.

The present invention therefore also contemplates that the antibody molecule of the invention or antigen binding fragment thereof is modified to have enhanced affinity to the FcγRIIIa receptor or has enhanced ADCC effector function as compared to the parent antibody. One way to achieve the enhanced ADCC is by introducing the amino acid substitutions 239D and 332E in the CH2 domain of the Fc part of the antibody molecule, for example into the murine or humanized 10B3 antibody. The cell killing activity of these antibodies may then be significantly increased or even detected and generated for the first time. In one embodiment, the amino acid substitutions are S239D and I332E.

An antibody molecule of the invention is capable of binding to human PSMA. The term "Prostate Specific Membrane Antigen" or "PSMA" are used interchangeably herein, and include variants, isoforms and species homologs of human PSMA. PSMA is also designated Glutamatcarboxypeptidase II, NAALADase I=N-Acetyl-L-aspartyl-L-glutamatpeptidase I, Folathydrolase I (FOLH1). Human PSMA has the UniProt accession number Q04609 (version 175 of 9 Dec. 2015). Accordingly, antibodies of the invention may, in certain cases, cross-react with PSMA from species other than human, or other proteins which are structurally related to human PSMA (e.g. human PSMA homologs). As mentioned before, a preferred embodiment of the present invention is the antibody 10B3 or a humanized version thereof. However, also other antibody molecules that bind to the same epitope as 10B3 are within the scope of the invention.

To determine the epitope, standard epitope mapping methods known in the art may be used. For example, fragments (peptides) of PMSA (e.g. synthetic peptides) that bind the antibody can be used to determine whether a candidate antibody or antigen-binding fragment thereof binds the same epitope. For linear epitopes, overlapping peptides of a defined length (e.g., 8 or more amino acids) are synthesized. The peptides can be offset by 1 amino acid, such that a series of peptides covering every 8 amino acid fragment of the PSMA protein sequence are prepared. Fewer peptides can be prepared by using larger offsets, e.g., 2 or 3 amino acids. In addition, longer peptides (e.g., 9-, 10- or 11-mers) can be synthesized. Binding of peptides to antibodies or antigen-binding fragments can be determined using standard methodologies including surface plasmon resonance (BIACORE) and ELISA assays. For examination of conformational epitopes, larger PSMA fragments can be used. Other methods that use mass spectrometry to define conformational epitopes have been described and can be (see, e.g., Baerga-Ortiz et al., *Protein Science* 11:1300-1308, 2002 and references cited therein). Still other methods for epitope determination are provided in standard laboratory reference works, such as Unit 6.8 ("Phage Display Selection and Analysis of B-cell Epitopes") and Unit 9.8 ("Identification of Antigenic Determinants Using Synthetic Peptide Combinatorial Libraries") of *Current Protocols in Immunology*, Coligan et al., eds., John Wiley & Sons. Epitopes can be confirmed by introducing point mutations or deletions into a known epitope, and then testing binding with one or more antibodies or antigen-binding fragments to determine which mutations reduce binding of the antibodies or antigen-binding fragments.

Also within the scope of the invention are antibody molecules that compete with an antibody molecule of the invention, such as 10B3, for binding to PSMA, e.g. to competitively inhibit binding of 10B3 to PSMA. To determine competitive inhibition, a variety of assays known to one of ordinary skill in the art can be employed. For example, cross-competition assays can be used to determine if an antibody or antigen-binding fragment thereof competitively inhibits binding to PSMA by another antibody or antigen-binding fragment thereof. These include cell-based methods employing flow cytometry or solid phase binding analysis. Other assays that evaluate the ability of antibodies or antigen-binding fragments thereof to cross-compete for PSMA molecules that are not expressed on the surface of cells, in solid phase or in solution phase, also can be used. An assay by which cross-competition can be tested is for example given in Example 10.

As mentioned herein the invention encompasses antibodies that have a reduced antigen shift compared to J591 when binding to PSMA. Such a reduced antigen shift may for example be assessed using the method essentially described in Example 10. In a preferred embodiment, such a reduced antigen shift is detected in PMSA-transfected Sp2/0 cells.

An antibody molecule according to the invention may have two chains, a shorter chain, which may in some embodiments be a light chain, and a main chain, which may in some embodiments also be addressed as the heavy chain. The antibody molecule is usually a dimer of these two chains.

An antibody molecule of the invention may preferably be a bispecific antibody molecule. The bispecific antibody molecule may comprise (i) a variable region comprising a heavy chain variable domain and a light chain variable domain as defined in any one of the preceding claims, wherein said variable region comprises a first binding site capable of binding to human prostate specific membrane antigen (PSMA) and (ii) a heavy chain variable region and a light chain variable region of an antibody molecule comprising a second binding site. It is understood that the binding site for PSMA is preferably a binding site of a PSMA-binding antibody of the invention described herein.

A "bispecific" or "bifunctional" antibody molecule is an antibody molecule that has two different epitope/antigen binding sites, and accordingly has binding specificities for two different target epitopes. These two epitopes may be epitopes of the same antigen or of different antigens. In contrast thereto a "bivalent antibody" may have binding sites of identical antigenic specificity.

A "bispecific antibody" may be an antibody molecule that binds one antigen or epitope with one of two or more binding arms, defined by a first pair of heavy and light chain or of main and shorter/smaller chain, and binds a different antigen or epitope on a second arm, defined by a second pair of heavy and light chain or of main and smaller chain. Such an embodiment of a bispecific antibody has two distinct antigen binding arms, in both specificity and CDR sequences. Typically, a bispecific antibody is monovalent for each antigen it binds to, that is, it binds with only one arm to the respective antigen or epitope. However, bispecific antibodies can also be dimerized or multimerized. For example, in the dimeric IgGsc format as described herein, the antibody may have two binding sites for each antigen. A bispecific antibody may be a hybrid antibody molecule, which may have a first binding region that is defined by a first light chain variable region and a first heavy chain variable region, and a second binding region that is defined by a second light chain variable region and a second heavy chain variable region. It is envisioned by the invention that one of these binding regions may be defined by a heavy/light chain pair. In the context of the present invention the bispecific antibody molecule may have a first binding site, defined by variable regions of a main chain and a smaller chain, and a second, different binding site defined by a variable region of a scFv fragment that is included in the main chain of the antibody molecule.

Methods of making a bispecific antibody molecule are known in the art, e.g. chemical conjugation of two different monoclonal antibodies or for example, also chemical conjugation of two antibody fragments, for example, of two Fab fragments. Alternatively, bispecific antibody molecules are made by quadroma technology, that is by fusion of the hybridomas producing the parental antibodies. Because of the random assortment of H and L chains, a potential mixture of ten different antibody structures are produced of which only one has the desired binding specificity.

The bispecific antibody molecule of the invention can act as a monoclonal antibody (MAb) with respect to each target. In some embodiments the antibody is chimeric, humanized or fully human. A bispecific antibody molecule may for example be a bispecific tandem single chain Fv, a bispecific Fab$_2$, or a bispecific diabody.

On the basis of the domains included in an antibody molecule of the invention the bispecific antibody molecule of the invention may comprise a Fab fragment, which may generally include a hinge region, a CH2 domain and a single chain Fv fragment. Such bispecific antibody molecules are termed "Fabsc"-antibody molecules and have been described for the first time in International patent application WO 2013/092001. More specifically, a "Fabsc" format antibody molecule as used here typically refers to a bispecific antibody molecule of the invention having a Fab fragment, which generally includes a hinge region, which is at the C-terminus of the Fab fragment linked to the N-terminus of a CH2 domain, of which the C-terminus is in turn linked to the N-terminus of a scFv fragment. Such a "Fabsc" does not or does not essentially comprise a CH3 domain. In this context, "not comprising" or "not essentially comprising" means that the antibody molecule does not comprise a full length CH3 domain. It preferably means that the antibody molecule comprises 10 or less, preferably 5 or less, preferably 3 or even less amino acids of the CH3 domain. An illustrative example for a Fabsc format antibody molecule is shown in FIG. 1A, another illustrative example for a Fabsc format antibody molecule is show in FIG. 12. In illustrative embodiments (cf. also FIG. 1A in this respect, an Fabsc antibody molecule of the invention may comprise a CH2 domain that lacks is ability to dimerize by the disulphide bonds that are formed by the cysteine residue at sequence position 226 of the hinge region and/or the cysteine residue at sequence position 229 of one of the hinge domains, according to the Kabat numbering [EU-Index]. Thus, in these embodiments, the cysteine residues at sequence position 226 and/or sequence position 229 is either removed or replaced, for example, by a serine residue. In addition, or alternatively, an "Fabsc" antibody molecule of the invention may also have an "Fc-attenuated" CH2 domain (that includes the hinge region). This "Fc-attenuation" is achieved by deleting and/or substituting (mutating) at least one of selected amino acid residues in the CH2 domain that are able to mediate binding to an Fc-receptor. In illustrative embodiments, the at least one amino acid residue of the hinge region or the CH2 domain that is able to mediate binding to Fc receptors and that is lacking or mutated, is selected from the group consisting of sequence position 228, 230, 231, 232, 233, 234, 235, 236, 237, 238, 265, 297, 327, and 330 (numbering of sequence positions according to the EU-index). In illustrative example, such an Fc-attenuated antibody molecule may contain at least one mutation selected from the group consisting of a deletion of amino acid 228, a deletion of amino acid 229, a deletion of amino acid 230, a deletion of amino acid 231, a deletion of amino acid 232, a deletion of amino acid 233, a substitution Glu233→Pro, a substitution Leu234→Val, a deletion of amino acid 234, a substitution Leu235→Ala, a deletion of amino acid 235, a deletion of amino acid 236, a deletion of amino acid 237, a deletion of amino acid 238, a substitution Asp265→Gly, a substitution Asn297→Gln, a substitution Ala327→Gln, and a substitution Ala330→Ser (numbering of sequence positions according to the EU-index, see in respect, for example, also FIG. 1O and FIG. 1P of International patent application WO 2013/092001). In the case of bispecific antibodies that activate T cells, e.g. against tumor cells, Fc-attenuation may be desired to prevent binding of the antibodies to Fc-receptor carrying cells which may lead to undesirable off-target activation of T cells.

In accordance with the publication of Coloma and Morrison (Nat Biotechnol 15:159-63, 1997), a bispecific antibody molecule of the invention may also have a CH3 domain, generally arranged C-terminally of the CH2 domain. Such a molecule is also referred to herein as an "IgGsc" format antibody molecule and means a bispecific antibody molecule of the invention having a Fab fragment, which generally includes a hinge region, which is at the C-terminus of the Fab fragment typically linked to the N-terminus of a CH2 domain, of which the C-terminus is in turn typically linked to the N-terminus of a CH3 domain, of which the C-terminus is in turn typically linked to the N-terminus of a scFv fragment. An illustrative example of an IgGsc format antibody molecule is shown in FIG. 1i, heavy and light chain sequences for such a molecule are molecule shown in FIGS. 11 and 13, respectively.

The antibody formats Fabsc and IgGsc have both in common that the N-terminal targeting part consists of "physiological" Fab- or Fab$_2$ regions, respectively, thereby avoiding the use of single chain moieties in this part of the molecule. If these formats are to be used for target cell restricted T cell activation, attenuation of Fc receptor (FcR) binding may be employed (if wanted or required) to prevent FcR mediated activation. This can be achieved e.g. by introduction of defined and well known mutations in the CH2 domain of the molecule as described in above and also in International patent application WO 2013/092001 and in Armour et al. Eur J Immunol 1999; 29:2613. Accordingly, also an IgGsc antibody molecule of the invention may have a CH2 domain (including the hinge region) in which at least one amino acid residue of the hinge region or the CH2 domain that is able to mediate binding to Fc receptors is lacking or mutated. As explained above, this residue in the CH2 and hinge region, respectively, may be selected from the group consisting of sequence position 228, 230, 231, 232, 233, 234, 235, 236, 237, 238, 265, 297, 327, and 330 (numbering of sequence positions according to the EU-index). However, due to the presence of the CH3 domain in the IgGsc molecule, two individual molecules will (spontaneously) homodimerize via the CH3 domain to form a tetravalent molecule (see again FIG. 1B in this respect). Thus, it is not necessary to delete or mutate the cysteine residues at sequence position 226 and/or sequence position 229 of the hinge region. Thus, such a tetrameric IgGsc antibody molecule of the invention may have a cysteine residue at sequence position 226 and/or at sequence position 229 of one of the respective hinge domain, in line with the Kabat numbering [EU-Index].

In line with the above disclosure of the bispecific antibody molecules that contain a set of CDR regions (for example, the CDR sequences of SEQ ID NO: 3 to SEQ ID NO:8 or a sequence with 80% sequence identity) that mediate PMSA binding and/or binding to squamous cancer cells, the antibody molecule of the present invention may comprise a second binding site that specifically binds to a receptor on an immune cell such as a T cell or an NK cells. This receptor present on the immune cell may be a receptor that is capable of activating the immune cell or of stimulating an immune response of the immune cell. The evoked immune response may preferably be a cytotoxic immune response. Such a suitable receptor may, for example, be CD3, the antigen specific T cell receptor (TCR), CD28, CD16, NKG2D, Ox40, 4-1 BB, CD2, CD5, programmed cell death protein 1 (PD-1) and CD95. Particularly preferred is an antibody molecule in which the second binding site binds to CD3, TCR or CD16. Most preferred is an antibody molecule, in which the second binding site specifically binds to CD3. A preferred antibody molecule comprises a second binding site that corresponds to the antigen binding site of the anti-CD3 antibody OKT3. The VH and VL sequences of an OKT3 antibody are depicted in FIG. 12. The amino acid sequence of the variable domain of the heavy chain and of the variable domain of the light chain of the antibody OKT3 are, for example, also described in Arakawa et al J. Biochem. 120, 657-662 (1996) and International Patent Application WO 2015/158868 (see SEQ ID NOS: 17 and 18 in the Sequence Listings of WO 2015/158868). Another preferred antibody molecule comprises a second binding site that corresponds to the antigen binding site of the anti-CD3 antibody UCHT1. The VH and VL sequences of a humanized UCHT1 antibody are depicted in FIG. 11 and, for example, also described in International Patent Application WO 2013/092001. Other examples of CD3 binding antibody molecules that can be used in the present invention include the antibody molecules described in European Patent 2 155 783 B1 or European Patent EP 2 155 788 B1 that are capable of binding to an epitope of human and *Callithrix jacchus, Saguinus oedipus* or *Saimiri sciureus* CD3F chain.

Accordingly, the bispecific antibody molecule of the invention may be a bispecific antibody molecule such as a Fabsc- and IgGsc-molecule that comprises a Fab fragment and a scFv fragment as described herein. In this molecule the first binding site may bind to PSMA and may be comprised in a Fab fragment as described herein and the second binding site (that may bind to an immune receptor) may be comprised in a scFv fragment. Alternatively, the first binding site that binds to PMSA is comprised in a single chain Fv fragment and the second binding site (that may bind to an immune receptor) is comprised in a Fab fragment.

In some embodiments, the bispecific antibody molecule of the invention does not by itself activate the immune cell, e.g. the T cell, upon binding, such as binding to CD3. Instead, only when both binding sites, e.g. the PMSA-specific binding sited and the CD3 specific binding site are bound to the receptor on the T cell and to PMSA on the target cell, the former may cross-link the activating receptor, triggering the effector cells to kill the specific target cell. Standard functional assays to evaluate the target cell-killing capability by lymphocytes in the presence and absence of an bispecific antibody molecule of the invention can be set up to assess and/or screen for the ability of the antibody molecule to activate the receptor to which it binds.

Without wishing to be bound to theory, it is generally held that bispecific CD3-binding antibodies of the invention do not activate T cells in the absence of target cells, since a monovalent CD3 stimulus is not sufficient to initiate effective T cell activation. However, in some cases, there may be some deviation from this assumed behavior. When UCHT1 was used here as a CD3 antibody within a bispecific Fabsc construct, some T cell activation was noted in the absence of PSMA expressing target cells. These findings were considerably more pronounced when the experiments were performed in the presence of stimulating bystander cells, such as SKW6.4 lymphoma cells. In contrast thereto, the inventors have surprisingly also found here that antibodies containing OKT3 and -surprisingly—also the IgGsc antibody comprising UCHT1 induce markedly attenuated off-target T cell activation. The unexpectedly low off-target activation by the IgGsc antibody comprising UCHT1 is at least in part explained by avidity measurements using CD3 expressing Jurkat cells. These experiments demonstrate that UCHT1 loses and OKT3 gains avidity if expressed in the IgGsc (rather than the Fabsc) format (cf. FIG. 8). When tested in a long term cytotoxic assay (Xelligence) against PSMA expressing 22RV1 cells the inventors of the present invention have surprisingly found following ranking for cytolytic activity: IgGsc(UCHT1)~Fabsc(UCHT1)>Fabsc(OKT3) >IgGsc(OKT3). Thus, within the IgGsc-format, UCHT1 may be the preferred CD3 antibody (favorable off-target activation and cytolytic activity), whereas within the Fabsc-format OKT3 may be preferred due to the undesirably high off-target activation by the UCHT1 containing Fabsc (cf. FIG. 9).

Figure 4A:
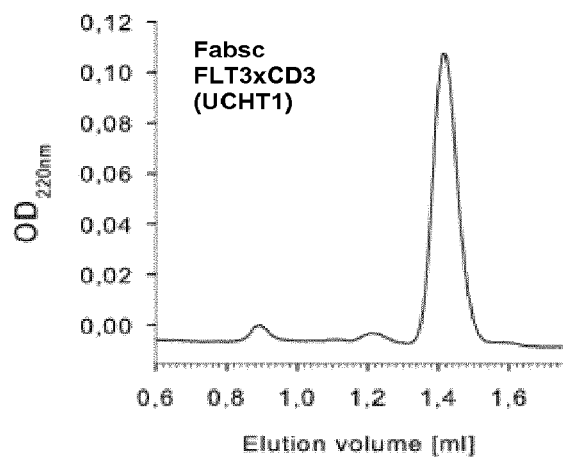
FIGS. 4A-4F depict multimerization and aggregation of different bispecific antibody formats.
Figure 4B:
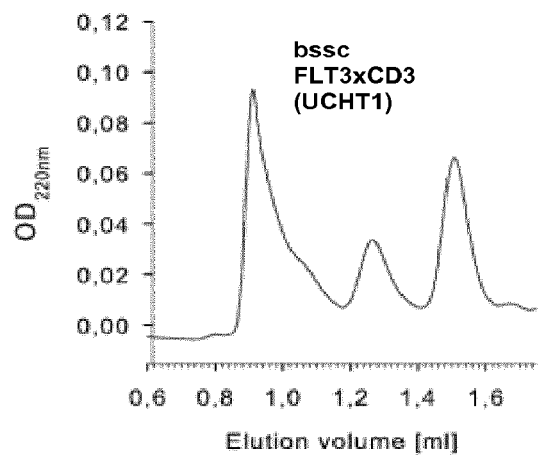
Figure 4C:
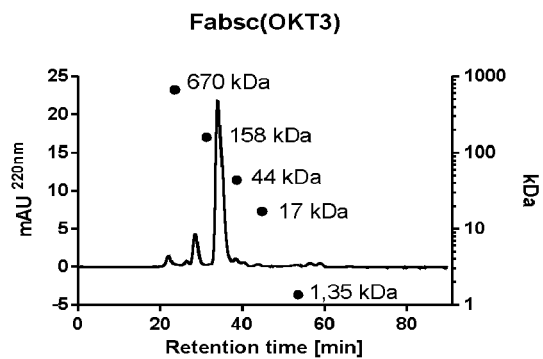

Regardless of the particular CD3 antibody used, clustering of bispecific antibodies on the surface of a T cell, induced by the interaction between targeting single chain fragments, may also lead to off-target T cell activation in the absence of a target cell. To prevent this phenomenon it may be desirable to use a Fab- or $Fab_2$-moiety, such as the one contained in the Fabsc- or IgGsc-format, respectively, rather than a single chain antibody as targeting part within a bispecific construct. Multimerization and aggregation of bispecific antibodies expressed in such formats is markedly reduced compared to that observed with bispecific single chain antibodies. FIGS. 4A and 4B show that aggregation of a bispecific single chain format with FLT3xCD3 specificity is less pronounced than that of an otherwise identical antibody in the bispecific single chain (bssc) or BiTE-format, as determined by size exclusion chromatography. FIGS. 4C-F show that, likewise, the tendency of the four PSMAxCD3 antibodies in the Fabsc as well as in the IgGsc format, to form multimers or aggregates is strongly reduced. Notably, the inventors of the present invention have surprisingly found that the formation of multimers is even considerably less pronounced in the two constructs containing the UCHT1 antibody compared to the constructs comprising the OKT3 antibody. In any case, it is believed that aggregation, if it occurs, is due to the CD3 effector part expressed as a single chain. It is believed and found here that the physiological Fab- and $Fab_2$ moieties at the N-terminal targeting part do not aggregate and thus it is believed that single chain clustering of the N-terminal targeting part, possibly resulting in T cell exhaustion in vivo, cannot occur in a respective antibody molecule of the invention.

Further, the inventors here foresee that the serum half-life of an antibody molecule is largely determined by the interaction of CH3 domains with the FcRn receptor. Since most bispecific antibodies are lacking this domain, their serum half-life may be rather short (several hours at best). In contrast, whole IgG molecules usually have a serum half-life of several days. Although IgG-based bispecific formats have been available for several years, they have been rarely used for construction of CD3-stimulating antibodies because it was thought that a bivalent CD3 stimulus may lead to off-target T cell activation. However, the inventors of the present invention have surprisingly found that the contrary is true for two different formats containing the UCHT1 antibody: off-target T cell activation by the Fabsc format is markedly higher than that by the antibody in the IgGsc-format. Without wishing to be bound to theory, it is believed that this is because the avidity of the CD3 moiety in the latter format is impaired (cf. again FIG. 8). This means, in the case of an antibody molecule comprising the variable region of UCHT1, the IgGsc-format surprisingly provides not only a markedly improved serum half-life but also reduced off-target T cell activation. Hence, if a prolonged serum half-life is desired, e.g. to avoid long term continuous infusion, a 10B3xUCHT1 bispecific antibody in the IgGsc format may be preferred, wherein the Fab moiety comprises the antigen binding site of an antibody derived from 10B3 and wherein the scFv moiety comprises the antigen binding site of an antibody derived from UCHT1. If a prolonged serum half-life is not desired, 10B3xOKT3 bispecific antibody in the Fabsc format may be preferred, wherein the Fab moiety comprises the antigen binding site of an antibody derived from 10B3 and wherein the scFv moiety comprises the antigen binding site of an antibody derived from OKT3.

Therefore, in other words, the present invention in an alternative aspect further pertains to a tetravalent and homodimeric bispecific antibody molecule (a bispecific antibody in the herein described IgGsc format) comprising in each monomer: (i) an N-terminal Fab fragment comprising a variable region comprising a heavy chain variable domain and a light chain variable domain, wherein said variable region comprises a first binding site capable of binding to an antigen; (ii) a C-terminal scFv fragment, comprising a heavy chain variable region and a light chain variable region of humanized UCHT1, and wherein (i) and (ii) are connected by a CH2 and CH3 domain In some embodiments the tetravalent bispecific antibody molecule of the invention is preferred, wherein at least one amino acid residue of the CH2 domain that is able to mediate binding to Fc receptors is lacking or mutated (see also herein elsewhere).

In some embodiments the tetravalent bispecific antibody molecule of the invention is preferred, wherein the Fab fragment is not a Fab fragment of a non-humanized, chimerized or humanized 10B3 or J591 antibody, preferably wherein the first binding site is not capable of binding to PSMA. Therefore, in some preferred embodiments the first binding site provided by the N-terminal Fab fragment is not specific for PSMA, but for a non-PSMA antigen, preferably a tumor associated antigen except PSMA. The term "tumor-associated antigen" relates to proteins that are under normal conditions, i.e. in a healthy subject, specifically expressed in a limited number of organs and/or tissues or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2 or 1. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably not or only rarely expressed in normal tissues or is mutated in tumor cells. Preferably, the tumor-associated antigen or the aberrant expression of the tumor-associated antigen identifies cancer cells. In the context of the present invention, the tumor-associated antigen that is expressed by a cancer cell in a subject, e.g., a patient suffering from a cancer disease is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, a tumor-associated antigen is presented in the context of MHC molecules by a cancer cell in which it is expressed.

Examples for TAA that may be useful in the present invention and that are not PSMA—according to preferred embodiments of the present aspect—are p53, ART-4, BAGE, beta-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap 100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A 10, MAGE-A11, or MAGE-A12, MAGE-B, MAGE-C, MART-1/Melan-A, MC1R, Myosin/m, MUCl", MUM-1, -2, -3, NA88-A, NFl, NY-ESO-1, NY-BR-1, p190 minor BCR-abL, Pml/RARa, PRAME, proteinase 3, PSA, RAGE, RU1 or RU2, SAGE, SART-1 or SART-3, SCGB3A2, SCP1, SCP2, SCP3, SSX, SURVIVIN, TEL/AML1, TPl/m, TRP-1, TRP-2, TRP-2/INT2, TPTE and WT.

In accordance with the present aspect of the invention a humanized UCHT1 is preferably a scFv fragment comprising the light chain variable region sequence and heavy chain variable region sequence as shown in SEQ ID NO: 11 starting with the the amino acid sequence DIQMT (SEQ ID NO: 17) . . . and ending with . . . VTVSS (SEQ IDS NO: 18) (as indicated in FIG. 11). Preferably the light chain variable region sequence and heavy chain variable region sequence in the scFv fragment are connected via a linker as depicted in FIG. 11 ("linker region").

It is noted in this context that it is within the scope of the invention that an antibody molecule may comprise one or more mutated amino acid residues. The terms "mutated", "mutant" and "mutation" in reference to a nucleic acid or a polypeptide refers to the exchange, deletion, or insertion of one or more nucleotides or amino acids, respectively, compared to the "naturally" occurring nucleic acid or polypeptide, i.e. to a reference sequence that can be taken to define the wild-type. For example, the variable domains of the antibody molecule 10B3 as obtained by immunization and as described herein may be taken as a wild-type sequence.

It is understood in this regard that the term "position", when used in accordance with the present invention, means the position of an amino acid within an amino acid sequence depicted herein. This position may be indicated relative to a resembling native sequence, e.g. a sequence of a naturally occurring IgG domain or chain. The term "corresponding" as used herein also includes that a position is not necessarily, or not only, determined by the number of the preceding nucleotides/amino acids. Thus, the position of a given amino acid in accordance with the present invention which may be substituted may vary due to deletion or addition of amino acids elsewhere in the antibody chain.

Thus, under a "corresponding position" in accordance with the present invention it is to be understood that amino acids may differ in the indicated number but may still have similar neighbouring amino acids. Said amino acids which may be exchanged, deleted or added are also encompassed by the term "corresponding position". In order to determine whether an amino acid residue in a given amino acid sequence corresponds to a certain position in the amino acid sequence of a naturally occurring immunoglobulin domain or chain, the skilled person can use means and methods well-known in the art, e.g., alignments, either manually or by using computer programs such as BLAST2.0, which stands for Basic Local Alignment Search Tool or ClustalW or any other suitable program which is suitable to generate sequence alignments.

In some embodiments a substitution (or replacement) is a conservative substitution. Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

Alanine (Ala), Glycine (Gly);
Aspartic acid (Asp), Glutamic acid (Glu);
Asparagine (Asn), Glutamine (Gln);
Arginine (Arg), Lysine (Lys);
Isoleucine (Ile), Leucine (Leu), Methionine (Met), Valine (Val);
Phenylalanine (Phe), Tyrosine (Tyr), Tryptophan (Trp);
Serine (Ser), Threonine (Thr); and
Cysteine (Cys), Methionine (Met)

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg→Gln; Asn→Asp, Lys, Arg, His; Asp→Asn; Cys→Ala; Gln→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

In some embodiments an antibody molecule according to the invention includes one or more amino acid residues, including two, three, four, five, six, seven, eight, nine, ten, eleven, twelve, thirteen, fourteen, fifteen, sixteen, seventeen or eighteen amino acid residues, that are mutated to prevent dimerization via cysteine residues or to modulate Fc-function (see above). In some of these embodiments one or more amino acid residue(s) of the CH2 domain and/or of the hinge region that is able to mediate binding to Fc receptors is mutated. If present, the one or more amino acid residue(s) able to mediate binding to Fc receptors may be an amino acid residue that is able to activate antibody dependent cellular cytotoxicity (ADCC) or complement-mediated cytotoxicity (CDC). In some embodiments a respective amino acid residue capable of mediating binding to Fc receptors is substituted by another amino acid, generally when comparing the sequence to the sequence of a corresponding naturally occurring domain in an immunoglobulin, such as an IgG In some embodiments such an amino acid residue capable of mediating binding to Fc receptors is deleted, generally relative to the sequence of a corresponding naturally occurring domain in an immunoglobulin, such as an IgG.

In some embodiments the one or more mutated, e.g. substituted or deleted, amino acid residues is/are an amino acid located at one of the positions 226, 228, 229, 230, 231, 232, 233, 234, 235, 236, 237, 238, 265, 297, 327, and 330. Again, the numbering of amino acids used corresponds to the sequence positions according to the Kabat numbering [EU-Index]. A corresponding deletion of an amino acid may for example be a deletion of amino acid 228, generally a proline in IgG, a deletion of amino acid 229, generally a cysteine in IgG, a deletion of amino acid 230, generally a proline in IgG, a deletion of amino acid 231, generally an alanine in IgG, a deletion of amino acid 232, generally a proline in IgG, a deletion of amino acid 233, generally a glutamic acid in IgG, a deletion of amino acid 234, generally a leucine in IgG, a deletion of amino acid 235, generally a leucine in IgG, a deletion of amino acid 236, generally a glycine in IgG, a deletion of amino acid 237, generally a glycine in IgG, a deletion of amino acid 238, generally a proline in IgG and a deletion of amino acid 265, generally an aspartic acid in IgG A corresponding substitution of an amino acid may for example be a substitution of amino acid 226, generally a cysteine in IgG, a substitution of amino acid 228, generally a proline in IgG, a substitution of amino acid 229, generally a cysteine in IgG, a substitution of amino acid 230, generally a proline in IgG, a substitution of amino acid 231, generally an alanine in IgG, a substitution of amino acid 232, generally a proline in IgG, a substitution of amino acid 233, generally a glutamic acid in IgG, a substitution of amino acid 234, generally a leucine in IgG, a substitution of amino acid 235, generally a leucine in IgG, a substitution of amino acid 265, generally an aspartic acid in IgG, a substitution of amino acid 297, generally an asparagine in IgG, a substitution of amino acid 327, generally an alanine in IgG, and a substitution of amino acid 330, generally an alanine in IgG A respective substitution may be one of substitution Cys226→Ser, substitution Cys229→Ser, substitution Glu233→Pro, substitution Leu234→Val, substitution Leu235→Ala, substitution Asp265→Gly, substitution Asn297→Gln, substitution Ala327→Gln, substitution Ala327→Gly, and substitution Ala330→Ser. As can be taken from the above, in some embodiments one or two of the cysteine residues at positions 226 and 229 in the hinge region are being substituted for another amino acid, for instance substituted for a serine residue. Thereby the formation of a disulphide bond with another main chain can be prevented. Further, and as also explained below, deleting and/or substituting (mutating) selected amino acid residues in the CH2 domain that is able to mediate binding to Fc-receptors can cause an antibody molecule of the invention to have less or no activity in terms of antibody-dependent cell-mediated cytotoxicity and fixation of complement.

Another type of amino acid variant of an antibody alters the original glycosylation pattern (if any) of the antibody molecule. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

In the context of the present invention, in some embodiments the portion of the main chain of the antibody molecule of the invention, which represents the Fc region of an immunoglobulin, is typically inert, or at least essentially of low influence, with regard to binding to Fc receptors. As said, this is achieved by deleting and/or substituting (mutating) at least one of selected amino acid residues in the CH2 domain that are able to mediate binding to an Fc-receptor. Such molecules are also referred to herein as "Fc-attenuated" antibody molecules or "Fc$^{ko}$" antibody molecules. The portion of an antibody chain according to the invention that can be taken to represent a portion of an Fc fragment, i.e. the CH2 domain, and, where present, the CH3 domain, thus might define a "scaffold" without providing a particular biological function such as an effector function, for example. However, it has been found in the present invention, that this scaffold may provide significant advantages in terms of purification, production efficiency and/or stability of the antibody molecules of the invention compared to known antibody molecules.

In some embodiments the recognition, and accordingly binding, of this Fc-corresponding portion to a given Fc receptor is of about 2-fold, about 5-fold, about 8-fold, about 10-fold, about 12-fold, about 15-fold, about 20-fold or lower than the Fc region of a naturally occurring immunoglobulin. In some embodiments this Fc-corresponding portion is entirely void of its ability of binding to Fc receptors. The binding of an antibody to Fc receptors, including determining a dissociation constant, can easily be determined by the skilled artisan using standard techniques such as surface plasmon resonance, e.g. using a Biacore™ measurement. Any other method of measuring biomolecular binding may likewise be used, which may for instance rely on spectroscopical, photochemical, photometric or radiological means. Examples for the corresponding detection methods are fluorescence correlation spectroscopy, photochemical crosslinking and the use of photoactive or radioactive labels respectively. Some of these methods may include additional separation techniques such as electrophoresis or HPLC.

Where required, a substitution or deletion of amino acid residues, as explained above, may be carried out to this effect. Suitable mutations can be taken from Armour et al. (Eur. J. Immunol. [1999]29, 2613-2624), for example. Further suitable positions for mutations to a sequence of an antibody chain can be taken from the crystal structure data published on the complex between FcγRIII and the human IgG1 Fc fragment (Sondermann et al., Nature [2000]406, 267-273). In addition to measuring the binding affinity as described above in order to assess the level of "Fc attenuation" or loss of binding affinity, it is also possible to functionally assess the (lack of the) ability to mediate binding to an Fc-receptor. In the case of antibody molecules which bind CD3 as one target, it is for example possible to assess the binding through the mitogenity of such CD3 binding antibody molecules on cells. The mitogenity is mediated by binding of CD3 antibodies to the Fc-receptors on accessory cells, such as monocytes. If an antibody molecule of the invention that has one binding site for CD3 does not show any mitogenic effect whereas the parent monoclonal anti-CD3 antibody that has a functional Fc part induces strong mitosis in T cells, it is clear that, due to the lack of mitosis, the antibody molecule of the invention lacks the ability for Fc binding and can thus be considered as a "Fc knock-out" molecule. Illustrative examples of a method of assessing anti-CD3 mediated mitogenity have been described by Davis, Vida & Lipsky (J. Immunol (1986) 137, 3758), and by Ceuppens, J L, & van Vaeck, F, (see J. Immunol. (1987) 139, 4067, or Cell. Immunol. (1989) 118, 136). Further illustrative suitable examples of an assay for assessing mitogenity of an antibody have been described by Rosenthal-Allieri et al. (Rosenthal-Allieri M A, Ticcioni M, Deckert M, Breittmeyer J P, Rochet N, Rouleaux M, and Senik A, Bernerd A, Cell Immunol. 1995 163(1):88-95) and Grosse-Hovest et al. (Grosse-Hovest L, Hartlapp I, Marwan W, Brem Q Rammensee H-Q and Jung Q Eur J Immunol. [2003] May; 33(5):1334-1340). In addition, the lack of Fc binding can be assessed by the ability of an antibody molecule of the invention to mediate one or more of the well-known effector functions of the Fc part.

As noted above, substitutions or deletions of cysteine residues may be carried out in order to introduce or to remove one or more disulfide bonds, including introducing or removing a potential or a previously existing disulfide bond. Thereby linkage between a main chain and a chain of lower weight/shorter length of an antibody molecule according to the invention may be controlled including established, strengthened or abolished. By introducing or removing one or more cysteine residues a disulfide bridge may be introduced or removed. As an illustrative example, a tetrameric antibody molecule according to the invention generally has one or more disulfide bonds that link two dimeric antibody molecules. One such disulfide bond is typically defined by a cysteine in the main chain of a first dimeric antibody molecule and a cysteine in the hinge region of a second dimeric antibody molecule. In this regard, in some embodiments an antibody according to the invention may include an amino acid substitution of a native cysteine residue at positions 226 and/or 229, relative to the sequence of a human IgG immunoglobulin according to the Kabat numbering [EU-Index], by another amino acid residue.

Substitutions or deletions of amino acid residues such as arginine, asparagine, serine, threonine or tyrosine residues may also be carried out to modify the glycosylation pattern of an antibody. As an illustrative example, an IgG molecule has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate. For human IgG, the core oligosaccharide typically consists of GlcNAc$_2$Man$_3$GlcNAc, with differing numbers of outer residues.

As indicated, besides binding of antigens/epitopes, an immunoglobulin is known to have further "effector functions", biological activities attributable to the Fc region (a native sequence Fc region or amino acid sequence variant Fc region) of an immunoglobulin, and vary with the immunoglobulin isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g., B cell receptors); and B cell activation. Exerting effector functions of an antibody generally involves recruiting effector cells. Several immunoglobulin effector functions are mediated by Fc receptors (FcRs), which bind the Fc region of an antibody. FcRs are defined by their specificity for immunoglobulin isotypes; Fc receptors for IgG antibodies are referred to as FcγR, for IgE as FcR, for IgA as FcαR and so on. Any of these effector functions (or the loss of such effector functions) such a CDC or ADCC can be used in order to evaluate whether an antibody molecule of the invention lacks the ability of Fc binding.

In this context, it is noted that the term "Fc receptor" or "FcR" defines a receptor, generally a protein that is capable of binding to the Fc region of an antibody. Fc receptors are found on the surface of certain cells of the immune system of an organism, for example natural killer cells, macrophages, neutrophils, and mast cells. In vivo Fc receptors bind to immunoglobulins that are immobilized on infected cells or present on invading pathogens. Their activity stimulates phagocytic or cytotoxic cells to destroy microbes, or infected cells by antibody-mediated phagocytosis or antibody-dependent cell-mediated cytotoxicity. Some viruses such as flaviviruses use Fc receptors to help them infect cells, by a mechanism known as antibody-dependent enhancement of infection. FcRs have been reviewed in Ravetch and Kinet, Annu. Rev. Immunol. 9: 457-92 (1991); Capel et al., Immunomethods 4: 25-34 (1994); and de Haas et al., J. Lab. Clin. Med. 126: 330-41 (1995).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202: 163 (1997) may be performed.

The term "complement system" is used in the art to refer a number of small proteins—called complement factors—found in blood, generally circulating as inactive precursors (pro-proteins). The term refers to the ability of this inalterable and not adaptable system to "complement" the capability of antibodies and phagocytic cells to clear pathogens such as bacteria, as well as antigen-antibody complexes, from an organism. An example of complement factors is the complex C1, which includes C1q and two serine protases, C1r and C1s. The complex C1 is a component of the CDC pathway. C1q is a hexavalent molecule with a molecular weight of approximately 460,000 and a structure likened to a bouquet of tulips in which six collagenous "stalks" are connected to six globular head regions. To activate the complement cascade, C1q has to bind to at least two molecules of IgG1, IgG2 or IgG3.

"Antibody-dependent cellular cytotoxicity" or ADCC refers to a form of cytotoxicity in which immunoglobulin molecules, bound onto Fc receptors (FcRs), present on certain cytotoxic cells—such as natural killer (NK) cells, neutrophils and macrophages—enable these cytotoxic effector cells to bind specifically to an antigen-bearing target cell and to subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9: 457-92 (1991). To assess ADCC activity of a molecule of interest, an in vitro ADCC assay, such as described in U.S. Pat. No. 5,500,362 or 5,821,337 may be carried out. Useful effector cells for such assays include, but are not limited to, peripheral blood mononuclear cells (PBMC) and natural killer (NK) cells. In some embodiments ADCC activity of the molecule of interest may be assessed in vivo, e.g., in an animal model such as disclosed in Clynes et al., PNAS USA 95: 652-656 (1998).

An antibody molecule of the invention may be produced using any known and well-established expression system and recombinant cell culturing technology, for example, by expression in bacterial hosts (prokaryotic systems), or eukaryotic systems such as yeasts, fungi, insect cells or mammalian cells. For example, an antibody molecule of the invention when being used in the "IgGsc" format, the antibody molecule can (of course) be produced as described by Coloma and Morrison (Nat Biotechnol 15:159-63, 1997) or as described in the Example Section of the present application. Likewise, an antibody molecule of the invention employed in the "Fabsc" format can be produced as described in International patent application WO 2013/092001 or as described here in the Example Section. An antibody molecule of the present invention may also be produced in transgenic organisms such as a goat, a plant or a XENOMOUSE transgenic mouse, an engineered mouse strain that has large fragments of the human immunoglobulin loci and is deficient in mouse antibody production. An antibody may also be produced by chemical synthesis.

For production of a recombinant antibody molecule of the invention, typically a polynucleotide encoding the antibody is isolated and inserted into a replicable vector such as a plasmid for further cloning (amplification) or expression. An illustrative example of a suitable expression system is a glutamate synthetase system (such as sold by Lonza Biologics), with the host cell being for instance CHO or NS0. A polynucleotide encoding the antibody is readily isolated and sequenced using conventional procedures. Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotides encoding the light and heavy chains may be inserted into separate vectors and transfected into the same host cell or, if desired both the heavy chain and light chain can be inserted into the same vector for transfection into the host cell. Both chains can, for example, be arranged, under the control of a dicistronic operon and expressed to result in the functional and correctly folded antibody molecule as described in Skerra, A. (1994) Use of the tetracycline promoter for the tightly regulated production of a murine antibody fragment in *Escherichia coli*, Gene 151, 131-135, or Skerra, A. (1994) A general vector, pASK84, for cloning, bacterial production, and single-step purification of antibody Fab fragments, Gene 141, 79-8. Thus according to one aspect of the present invention there is provided a process of constructing a vector encoding the light and/or heavy chains of an antibody or antigen binding fragment thereof of the invention, which method includes inserting into a vector, a polynucleotide encoding either a light chain and/or heavy chain of an antibody molecule of the invention.

When using recombinant techniques, the antibody molecule can be produced intracellularly, in the periplasmic space, or directly secreted into the medium (cf. also Skerra 1994, supra). If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E coli*. The antibody can also be produced in any oxidizing environment. Such an oxidizing environment may be provided by the periplasm of Gram-negative bacteria such as *E. coli*, in the extracellular milieu of Gram-positive bacteria or in the lumen of the endoplasmatic reticulum of eukaryotic cells (including animal cells such as insect or mammalian cells) and usually favors the formation of structural disulfide bonds. It is, however, also possible to produce an antibody molecule of the invention in the cytosol of a host cell such as *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi M, Seifert C, Hunte C. (2002) "High level production of functional antibody Fab fragments in an oxidizing bacterial cytoplasm." J. Mol. Biol. 315, 1-8).

The antibody molecule produced by the cells can be purified using any conventional purification technology, for example, hydroxylapatite chromatography, gel electrophoresis, dialysis, and affinity chromatography, with affinity chromatography being one preferred purification technique. Antibody molecules may be purified via affinity purification with proteins/ligands that specifically and reversibly bind constant domains such as the CH1 or the CL domains. Examples of such proteins are immunoglobulin-binding bacterial proteins such as Protein A, Protein Q Protein A/G or Protein L, wherein Protein L binding is restricted to antibody molecules that contain kappa light chains. An alternative method for purification of antibodies with κ-light chains is the use of bead coupled anti kappa antibodies (KappaSelect). The suitability of protein A as an affinity ligand depends on the species and isotype of any immunoglobulin Fc domain that is present in the antibody. Protein A can be used to purify antibodies (Lindmark et al., J. Immunol. Meth. 62: 1-13 (1983)). Protein G is recommended for all mouse isotypes and for human gamma3 (Guss et al., EMBO J. 5: 15671575 (1986)). The choice of the purification method that is used for a particular antibody molecule of the invention is within the knowledge of the person of average skill in the art.

It is also possible to equip one of the chains of the antibody molecule of the invention with one or more affinity tags. Affinity tags such as the Strep-tag® or Strep-tag® II (Schmidt, T. G M. et al. (1996) J. Mol. Biol. 255, 753-766), the myc-tag, the FLAG™-tag, the His6-tag or the HA-tag allow easy detection and also simple purification of the recombinant antibody molecule.

Turning now to nucleic acids of the invention, a nucleic acid molecule encoding one or more chains of an antibody according to the invention may be any nucleic acid in any possible configuration, such as single stranded, double stranded or a combination thereof. Nucleic acids include for instance DNA molecules, RNA molecules, analogues of the DNA or RNA generated using nucleotide analogues or using nucleic acid chemistry, locked nucleic acid molecules (LNA), and protein nucleic acids molecules (PNA). DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label.

In some embodiments a nucleic acid sequence encoding a chain, such as a main chain and/or a smaller chain of an antibody according to the invention is included in a vector such as a plasmid. Where a substitution or deletion is to be included in an antibody chain, when compared to a naturally occurring domain or region of an antibody, the coding sequence of the respective native domain/region, e.g. included in the sequence of an immunoglobulin, can be used as a starting point for the mutagenesis. For the mutagenesis of selected amino acid positions, the person skilled in the art has at his disposal the various established standard methods for site-directed mutagenesis. A commonly used technique is the introduction of mutations by means of PCR (polymerase chain reaction) using mixtures of synthetic oligonucleotides, which bear a degenerate base composition at the desired sequence positions. For example, use of the codon NNK or NNS (wherein N=adenine, guanine or cytosine or thymine; K=guanine or thymine; S=adenine or cytosine) allows incorporation of all 20 amino acids plus the amber stop codon during mutagenesis, whereas the codon VVS limits the number of possibly incorporated amino acids to 12, since it excludes the amino acids Cys, Ile, Leu, Met, Phe, Trp, Tyr, Val from being incorporated into the selected position of the polypeptide sequence; use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated at a selected sequence position. In this respect it is noted that codons for other amino acids (than the regular 20 naturally occurring amino acids) such as selenocystein or pyrrolysine can also be incorporated into a nucleic acid of an antibody molecule. It is also possible, as described by Wang, L., et al. (2001) Science 292, 498-500, or Wang, L., and Schultz, P. G (2002) Chem. Comm. 1, 1-11, to use "artificial" codons such as UAG which are usually recognized as stop codons in order to insert other unusual amino acids, for example o-methyl-L-tyrosine or p-aminophenylalanine.

The use of nucleotide building blocks with reduced base pair specificity, as for example inosine, 8-oxo-2'deoxyguanosine or 6(2-deoxy-β-D-ribofuranosyl)-3,4-dihydro-8H-pyrimin-do-1,2-oxazine-7-one (Zaccolo et al. (1996) J. Mol. Biol. 255, 589-603), is another option for the introduction of mutations into a chosen sequence segment. A further possibility is the so-called triplet-mutagenesis. This method uses mixtures of different nucleotide triplets, each of which codes for one amino acid, for incorporation into the coding sequence (Virnekas B, et al., 1994 Nucleic Acids Res 22, 5600-5607).

A nucleic acid molecule encoding a chain, such as a main chain and/or a smaller chain of an antibody according to the invention can be expressed using any suitable expression system, for example in a suitable host cell or in a cell-free system. The obtained antibody molecule may be enriched by means of selection and/or isolation.

The invention also provides a pharmaceutical composition that includes an antibody molecule of the invention and, optionally a pharmaceutically acceptable excipient.

The antibody molecule according to the invention can be administered via any parenteral or non-parenteral (enteral) route that is therapeutically effective for proteinaceous drugs. Parenteral application methods include, for example, intracutaneous, subcutaneous, intramuscular, intratracheal, intranasal, intravitreal or intravenous injection and infusion techniques, e.g. in the form of injection solutions, infusion solutions or tinctures, as well as aerosol installation and inhalation, e.g. in the form of aerosol mixtures, sprays or powders. An overview about pulmonary drug delivery, i.e. either via inhalation of aerosols (which can also be used in intranasal administration) or intracheal instillation is given by J. S. Patton et al. The lungs as a portal of entry for systemic drug delivery. Proc. Amer. Thoracic Soc. 2004 Vol.

1 pages 338-344, for example). Non-parenteral delivery modes are, for instance, orally, e.g. in the form of pills, tablets, capsules, solutions or suspensions, or rectally, e.g. in the form of suppositories. Antibody molecules of the invention can be administered systemically or topically in formulations containing conventional non-toxic pharmaceutically acceptable excipients or carriers, additives and vehicles as desired.

In one embodiment of the present invention the pharmaceutical is administered parenterally to a mammal, and in particular to humans. Corresponding administration methods include, but are not limited to, for example, intracutaneous, subcutaneous, intramuscular, intratracheal or intravenous injection and infusion techniques, e.g. in the form of injection solutions, infusion solutions or tinctures as well as aerosol installation and inhalation, e.g. in the form of aerosol mixtures, sprays or powders. A combination of intravenous and subcutaneous infusion and/or injection might be most convenient in case of compounds with a relatively short serum half-life. The pharmaceutical composition may be an aqueous solution, an oil-in water emulsion or a water-in-oil emulsion.

In this regard it is noted that transdermal delivery technologies, e.g. iontophoresis, sonophoresis or microneedle-enhanced delivery, as described in Meidan V M and Michniak B B 2004 Am. J. Ther. 11(4): 312-316, can also be used for transdermal delivery of an antibody molecule described herein. Non-parenteral delivery modes are, for instance, oral, e.g. in the form of pills, tablets, capsules, solutions or suspensions, or rectal administration, e.g. in the form of suppositories. The antibody molecules of the invention can be administered systemically or topically in formulations containing a variety of conventional non-toxic pharmaceutically acceptable excipients or carriers, additives, and vehicles.

The dosage of the antibody molecule applied may vary within wide limits to achieve the desired preventive effect or therapeutic response. It will, for instance, depend on the affinity of the antibody molecule for a chosen target as well as on the half-life of the complex between the antibody molecule and the ligand in vivo. Further, the optimal dosage will depend on the biodistribution of the antibody molecule or a conjugate thereof, the mode of administration, the severity of the disease/disorder being treated as well as the medical condition of the patient. For example, when used in an ointment for topical applications, a high concentration of the antibody molecule can be used. However, if wanted, the antibody molecule may also be given in a sustained release formulation, for example liposomal dispersions or hydrogel-based polymer microspheres, like PolyActive™ or Octo-DEX™ (cf. Bos et al., Business Briefing: Pharmatech 2003: 1-6). Other sustained release formulations available are for example PLGA based polymers (PR pharmaceuticals), PLA-PEG based hydrogels (Medincell) and PEA based polymers (Medivas).

Accordingly, the antibody molecules of the present invention can be formulated into compositions using pharmaceutically acceptable ingredients as well as established methods of preparation (Gennaro, A. L. and Gennaro, A. R. (2000) Remington: The Science and Practice of Pharmacy, 20th Ed., Lippincott Williams & Wilkins, Philadelphia, PA). To prepare the pharmaceutical compositions, pharmaceutically inert inorganic or organic excipients can be used. To prepare e.g. pills, powders, gelatin capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

The antibody molecule may be suitable for and may be used in the treatment or prevention of a disease. Accordingly, in some embodiments, an antibody molecule according to the invention may be used in a method of treating and/or preventing a medical condition such as a disorder or disease. Similarly, the antibody molecule of the present invention can be used in the treatment of a disease. The disease to be treated or prevented may be a proliferative disease. Such a proliferative disease may preferably be tumor or cancer. Due to the ability of the antibody molecule of the invention to bind PMSA, this antibody molecule can be used to treat cancer that consists of cells that express PSMA, such as primary and metastatic prostate cancer cells (cf., and the neovasculature of a wide spectrum of malignant neoplasms such as conventional (clear cell) renal carcinoma, transitional cell carcinoma of the urinary bladder, testicular embryonal carcinoma, colonic adenocarcinoma, neuroendocrine carcinoma, glioblastoma multiforme, malignant melanoma, pancreatic duct carcinoma, non-small cell lung carcinoma, soft tissue sarcoma, and breast carcinoma (see in this context, Chang S S et al. Five different anti prostate specific membrane antigen (PSMA) antibodies confirm PSMA expression in tumor associated neovasculature. Cancer Res 1999; 59:3192). Thus, the antibody molecule of the invention may in one aspect be used in the treatment of a solid cancer, such as prostate cancer, colon cancer, mammary cancer, pancreatic cancer or glioblastoma. However, due to the surprising finding that the antibody of the invention also binds to squamous cells, the antibody molecule of the invention may in another aspect be preferably also be used in the treatment of squamous cell carcinoma of different origins (including but not limited to): carcinoma of the skin, head and neck, esophagus, lung and cervix uteri.

The subject to be treated with the fusion protein can be a human or non-human animal. Such an animal is preferably a mammal, for instance a human, pig, cattle, rabbit, mouse, rat, primate, goat, sheep, chicken, or horse, most preferably a human.

The antibody molecule of the invention may also be used in the diagnosis of a disease, such as a disease as described herein. The antibody molecule may for this purpose be labeled with a suitable detectable signaling label. Such a labeled antibody molecule may permit detection or quantitation of PSMA level or cancer such as prostate cancer, colon cancer, mammary cancer, pancreatic cancer or glioblastoma squamous cell carcinoma as well as squamous cell carcinomas of different origin as listed above in a sample or subject. When designated for in vivo use, said detectable signaling label is preferably detectable in vivo.

The labelled antibody molecule may be used in an immune-imaging technique. The detectable signaling label may then be selected, for instance, based on the immuno-imaging technique employed for the diagnosis, for example, gamma-emitting radionuclide (or gamma-emitter) in case of gamma camera-imaging technique/SPECT, metal or positron emitter in case of MRI or PET imaging techniques, respectively. In this regard, one or more detectable signaling labels of the disclosure include gamma camera-imagable agents, PET-imagable agents and MRI-imagable agents, such as, radionuclides, fluorescers, fluorogens, chromophores, chromogens, phosphorescers, chemiluminescers and bioluminescers.

A suitable detectable signaling label may be a radionuclide. Said radionuclide may selected from the group consisting of $^{3}H$, $^{14}C$, $^{35}S$, $^{99}Tc$, $^{123}I$, $^{125}I$, $^{131}I$, $^{m}In$, $^{97}Ru$, $^{67}Ga$, $^{68}Ga$, $^{72}As$, $^{89}Zr$ and $^{201}Tl$.

A suitable detectable signaling label may also be fluorophore or fluorogen. Said fluorophore or fluorogen may be selected from the group consisting of fluorescein, rhodamine, dansyl, phycoerythrin, phycocyanin, allophycocyanin, o-phthaldehyde, fluorescamine, fluorescein derivative, Oregon Green, Rhodamine Green, Rhodol Green or Texas Red.

The labelled antibody molecule may be coupled either directly or indirectly to a detectable signaling label. For example, the antibody molecule may be coupled either directly (e.g. via tyrosine residues of the antibody molecule) or indirectly (e.g. via a linker—as a metal chelating agent) to a detectable signaling label. In some other embodiments, the antibody molecule may be coupled to a molecule that is able to be coupled (either in vitro or in vivo) to the detectable signaling label at the time and place of use.

A detectable signaling label may be bound to the antibody molecule through one or more diethylenetriaminepentaacetic acid (DTPA) residues that are coupled to the antibody molecule.

Also contemplated by the invention is an in vitro method of detecting or diagnosing a disease defined herein. Such a method may comprise contacting a sample obtained from a subject with a preferably labelled antibody molecule of the invention. The sample may be a blood, urine or cerebrospinal fluid sample, but may preferably be tissue sample or a biopsy sample. The disease to be detected or diagnosed is preferably prostate cancer, colon cancer, mammary cancer, pancreatic cancer, glioblastoma or squamous cell carcinoma, most preferably squamous cell carcinoma.

The present invention is further characterized by the following items

Item 1. An antibody molecule or an antigen-binding fragment thereof, capable of binding to human prostate specific membrane antigen (PSMA), comprising: (i) a heavy chain variable domain comprising the CDRH1 region set forth in SEQ ID NO: 03 (GFTFSDFYMY), the CDRH2 region set forth in SEQ ID NO: 04 (TISDGGGYT-SYPDSVKG), and the CDRH3 region set forth in SEQ ID NO: 05 (GLWLRDALDY) or comprising a CDRH1, CDRH2 or CDRH3 sequence having at least 75% sequence identity or at least 80% sequence identity with SEQ ID NO: 03, SEQ ID NO: 04, or SEQ ID NO: 05; and (ii) a light chain variable domain comprising the CDRL1 region set forth in SEQ ID NO: 06 (SASSSISSNYLH), the CDRL2 region set forth in SEQ ID NO: 07 (RTSNLAS), and the CDRL3 region set forth in SEQ ID NO: 08 (QQGSYIPFT) or comprising a CDRL1, CDRL2 or CDRL3 sequence having at least 75% sequence identity or at least 80% sequence identity with SEQ ID NO: 06, SEQ ID NO: 07, or SEQ ID NO: 08.

Item 2. The antibody molecule or antigen binding fragment thereof of item 1, wherein the heavy chain variable region comprises the amino acid sequence having a sequence identity of at least 90% to the amino acid sequence set forth in SEQ ID NO: 01 or 09.

Item 3. The antibody molecule or antigen binding fragment thereof of item 1 or 2, wherein the light chain variable region comprises the amino acid sequence having a sequence identity of at least 90% to the amino acid sequence set forth in SEQ ID NO: 02 or 10.

Item 4. The antibody molecule or antigen binding fragment thereof of any one of the preceding items, wherein the antibody is selected from the group consisting of a scFv, a univalent antibody lacking a hinge region, a minibody, a Fab fragment, a Fab' fragment, a F(ab')$_2$ fragment, and a whole antibody.

Item 5. The antibody molecule or antigen binding fragment thereof of any one of the preceding items comprising a human IgG constant domain.

Item 6. The antibody molecule or antigen binding fragment thereof of any one of the preceding items comprising a CH1 domain.

Item 7. The antibody molecule or antigen binding fragment thereof of any one of the preceding items comprising an Fc region.

Item 8. The antibody molecule or antigen binding fragment thereof of any one of the preceding items, wherein the antibody has antibody-dependent cell mediated cytotoxicity (ADCC) effector function.

Item 9. The antibody molecule or antigen binding fragment thereof of item 8 having enhanced affinity to the FcγRIIIa receptor or has enhanced ADCC effector function as compared to the parent antibody.

Item 10. The antibody molecule or antigen binding fragment thereof of any one of the preceding items comprising a heavy chain and a light chain and at least one amino acid substitution in the constant region relative to a parent antibody, wherein said at least one amino acid substitution comprises the amino acid substitutions S239D and I332E, wherein the positional numbering is according to the EU index.

Item 11. An antibody molecule or an antigen-binding fragment thereof, capable of binding to human PSMA that is able to compete with the binding of an antibody molecule or antigen-binding fragment thereof of item 1 to human PSMA.

Item 12. The antibody molecule or antigen binding fragment thereof of any one of the preceding items, wherein the antibody molecule or antigen-binding fragment thereof does not compete with the binding of J591 to human PSMA.

Item 13. The antibody molecule or antigen binding fragment thereof of any one of the preceding items, wherein the antibody molecule or antigen-binding fragment thereof has a reduced induction of antigen shift when binding to PSMA than J591.

Item 14. The antibody molecule or antigen binding fragment thereof of item 13, wherein the antigen shift is induced in PMSA-transfected Sp2/0 cells.

Item 15. The antibody molecule or antigen binding fragment thereof of any one of the preceding claims, wherein the antibody molecule or antigen-binding fragment thereof further binds to squamous cell carcinoma (SCC) cells.

Item 16. A bispecific antibody molecule comprising (i) a variable region comprising a heavy chain variable domain and a light chain variable domain as defined in any one of the preceding items, wherein said variable region comprises a first binding site capable of binding to human prostate specific membrane antigen (PSMA); and (ii) a heavy chain variable region and a light chain variable region of an antibody molecule comprising a second binding site.

Item 17. The antibody molecule of item 16, wherein the first binding site and the second binding site bind to different binding partners.

Item 18. The antibody molecule of any item 16 or 17, wherein the first or second binding site binds to a T cell or natural killer (NK) cell specific receptor molecule.

Item 19. The antibody molecule of any one of items 16 to 18, wherein the T-cell- or NK cell specific receptor molecule is one of CD3, T cell receptor (TCR), CD28, CD16, NKG2D, Ox40, 4-1 BB, CD2, CD5, PD-1 and CD95.

Item 20. The antibody molecule of any one of item 19, wherein the TCR is TCR (alpha/beta) or TCR (gamma/delta).

Item 21. The antibody molecule of item 19, wherein the T-cell- or NK cell specific receptor molecule is CD3.

Item 22. The antibody molecule of item 21, wherein the heavy chain variable region and a light chain variable region of an antibody molecule comprising a second binding site is the heavy chain variable region and a light chain variable region of OKT3 or UCHT1.

Item 23. The antibody molecule of any one of items 15 to 21, wherein (i) the first binding site is comprised in a Fab fragment and the second binding site is comprised in a scFv fragment; or (ii) the first binding site is comprised in a single chain Fv fragment and the second binding site is comprised in a Fab fragment.

Item 24. The antibody molecule of item 23, wherein the Fab fragment and the single chain Fv fragment are linked via a CH2 domain and/or a CH3 domain.

Item 25. The antibody molecule of item 24, wherein at least one amino acid residue of the CH2 domain that is able to mediate binding to Fc receptors is lacking or mutated.

Item 26. The antibody molecule of item 24 or 25, wherein one or more amino acid residues of sequence positions 226, 228, and 229 is lacking or mutated (numbering of sequence positions according to the EU-index).

Item 27. The antibody molecule of any one of item 24 to 26 wherein the Fab fragment is linked to the CH2 domain via the heavy chain CH1 and VH domains of the Fab fragment or via the CL and VL light chain domains of the Fab fragment.

Item 28. The antibody molecule of item 27, wherein the heavy chain domains of the Fab fragment or the light chain domains of the Fab fragment are arranged at the N-terminus of the polypeptide chain of the antibody molecule.

Item 29. The antibody molecule of any of the preceding items, wherein the Fab fragment comprises a hinge region.

Item 30. The antibody molecule of any one of items 24 to 29, wherein the at least one amino acid residue of the CH2 domain that is able to mediate binding to Fc receptors is lacking or mutated, is selected from the group consisting of sequence position 230, 231, 232, 233, 234, 235, 236, 237, 238, 265, 297, 327, and 330 (numbering of sequence positions according to the EU-index).

Item 31. The antibody molecule of any one of items 24 to 30, wherein a cysteine at one or both of positions 226 and 229 is replaced by a different amino acid.

Item 32. The antibody molecule of any one of items 24 to 31 comprising a Fab fragment, a CH2 domain and a scFv fragment, wherein the Fab fragment comprises a hinge region.

Item 33. The antibody molecule of item 32, wherein the Fab fragment is a Fab fragment of a humanized 10B3 antibody and/or wherein the scFv fragment comprises a heavy chain variable region and a light chain variable region from OKT3 antibody.

Item 34. The antibody molecule of item 33, wherein the heavy chain of the antibody molecule has a sequence as set forth in SEQ ID NO: 12 and/or wherein the light chain of the antibody molecule has a sequence set forth in SEQ ID NO: 13.

Item 35. The antibody molecule of any one of items 24 to 31 comprising a Fab fragment, a CH2 domain, a CH3 domain and a scFv fragment, wherein the Fab fragment comprises a hinge region.

Item 36. The antibody molecule of item 35, wherein the Fab fragment is a Fab fragment of a humanized 10B3 antibody and/or wherein the scFv fragment comprises a heavy chain variable region and a light chain variable region from a humanized UCHT1 antibody.

Item 37. The antibody molecule of item 36, wherein the heavy chain of the antibody molecule has a sequence as set forth in SEQ ID NO: 11 and/or wherein the light chain of the antibody molecule has a sequence set forth in SEQ ID NO: 13.

Item 38. The antibody molecule of any one of items 35 to 37, wherein the antibody molecule is a tetrameric antibody molecule.

Item 39. The antibody molecule of any one of items 16 to 23, wherein the antibody molecule is a bispecific tandem single chain Fv, a bispecific Fab$_2$, or a bispecific diabody.

Item 40. A pharmaceutical composition comprising an antibody molecule or an antigen-binding fragment thereof as defined in any of the preceding items.

Item 41. An antibody molecule or an antigen-binding fragment thereof as defined in any of items 1 to 39 for use in the diagnosis or treatment of a disease.

Item 42. The antibody molecule or antigen-binding fragment thereof for the use of item 41, where the disease is a proliferatory disease.

Item 43. The antibody molecule or antigen-binding fragment thereof for the use of item 42, wherein the proliferatory disease is cancer.

Item 44. The antibody molecule or antigen-binding fragment thereof for the use of item 43, wherein the cancer is prostate cancer, colorectal cancer, cancer of the stomach, lung carcinoma, osteosarcoma, mammary cancer, pancreatic cancer or glioblastoma.

Item 45. The antibody molecule or antigen-binding fragment thereof for the use of item 43, wherein the cancer is squamous cell carcinoma.

Item 46. An in vitro method of diagnosing a disease comprising contacting a sample obtained from a subject with an antibody molecule or an antigen-binding fragment thereof as defined in any one of items 1 to 39.

Item 47. The in vitro method of item 46, wherein the sample is a tissue sample or a biopsy sample.

Item 48. The in vitro method of item 46 or 47, wherein the disease is cancer, preferably prostate cancer, colorectal cancer, cancer of the stomach, lung carcinoma, osteosarcoma, mammary cancer, pancreatic cancer, glioblastoma or squamous cell carcinoma.

Item 49. A nucleic acid molecule encoding an antibody molecule or an antigen-binding fragment thereof as defined in any of items 1 to 39.

Item 50. A vector comprising the nucleic acid molecule of item 49.

Item 51. A host cell comprising a nucleic acid molecule of item 49 or a vector of item 50.

Item 52. A method of producing an antibody molecule or an antigen-binding fragment thereof of any one of items 1 to 39, comprising expressing a nucleic acid encoding the antibody molecule under conditions allowing expression of the nucleic acid.

Item 53. The method of item 52 wherein the antibody molecule or antigen-binding fragment thereof is expressed in a host cell or a cell-free system.

BRIEF DESCRIPTION OF THE SEQUENCE LISTING

SEQ ID NO: 01: heavy chain variable domain of murine 10B3 antibody (amino acid sequence).
SEQ ID NO: 02: light chain variable domain of murine 10B3 antibody (amino acid sequence).
SEQ ID NO: 03: CDRH1 of murine 10B3 antibody (amino acid sequence).
SEQ ID NO: 04: CDRH2 of murine 10B3 antibody (amino acid sequence).
SEQ ID NO: 05: CDRH3 of murine 10B3 antibody (amino acid sequence).
SEQ ID NO: 06: CDRL1 of murine 10B3 antibody (amino acid sequence).
SEQ ID NO: 07: CDRL2 of murine 10B3 antibody (amino acid sequence).
SEQ ID NO: 08: CDRL3 of murine 10B3 antibody (amino acid sequence).
SEQ ID NO: 09: heavy chain variable domain of humanized 10B3 antibody (amino acid sequence).
SEQ ID NO: 10: light chain variable domain of humanized 10B3 antibody (amino acid sequence).
SEQ ID NO: 11: heavy chain of the humanized h10B3 X humanized hUCHT1 bispecific IgGsc format antibody molecule
SEQ ID NO: 12: heavy chain of the humanized h10B3 X murine OKT3 bispecific Fabsc format antibody molecule
SEQ ID NO: 13: kappa light chain of humanized 10B3 antibody
SEQ ID NO: 14: illustrative example of a mutated CDRH1 of murine 10B3 antibody (amino acid sequence) having at least 75% sequence identity to SEQ ID NO: 3.
SEQ ID NO: 15: amino acid sequence of the variable domain of the heavy chain of the antibody J519.
SEQ ID NO: 16: the amino acid sequence of the variable domain of the light chain of the antibody J519.

EXPERIMENTAL EXAMPLES

The invention is further illustrated by the following non-limiting Examples.

Example 1: Generation, Identification and Production of the 10B3 Antibody

The antibody 10B3 was generated after immunization of female BALB/c mice with irradiated PSMA transfected Sp2/0 Ag14 cells (the Sp2/0-Ag14 cells were obtained from ATCC where they are commercially available under the name ATCC© CRL-1581™) Four days after the last immunization spleen cells were fused with the transfected Sp2/0 cells and cultured in HAT selection medium. Supernatants of growing hybridoma cells were screened for production of PSMA antibodies by flow cytometry using PSMA transfected- and untransfected Sp2/0 cells. After subcloning by limiting dilution a stable monoclonal hybridoma cell line was obtained. For antibody production hybridoma cells were adapted to advanced DMEM medium (Gibco, Thermo Scientific, Waltham, MA, USA02451), supplemented with 1% FCS (Biochrom GmbH, Berlin, Germany) to avoid contamination with bovine IgG during purification. The antibody was isolated from cell culture supernatants by a Protein-A affinity chromatography and the isotype of the purified antibody was identified as IgG2b/kappa (Rapid Mouse-Monoclonal Isotyping Kit, BioAssay Works, Ijamsville, MD, 21754). The sequence of the variable heavy chain (shown in SEQ ID NO: 1 and FIG. 10A) and of the variable light chain shown (shown in SEQ ID NO: 2 and FIG. 10B) was determined by Alvedron GmbH, Freiburg, Germany.

Example 2: Generation of a Humanized 10B3 Antibody

The 10B3 antibody was humanized by grafting the CDR regions into the germline sequences of the human variable κ light sequence IGKV3-20*02 (this sequence is deposited in the IMGT/LIGM-database under accession number L37729, see also Ichiyoshi Y., Zhou M., Casali P. A human anti-insulin IgG autoantibody apparently arises through clonal selection from an insulin-specific 'germ-line' natural antibody template. Analysis by V gene segment reassortment and site-directed mutagenesis' *J. Immunol.* 154(1):226-238 (1995) and the variable heavy chain sequence IGHV3-11*06 (this sequence is deposited in the IMGT/LIGM-database under accession number AF064919, see also Watson C. T., et al. Complete haplotype sequence of the human immunoglobulin heavy-chain variable, diversity, and joining genes and characterization of allelic and copy-number variation. *Am. J. Hum. Genet.* 92(4):530-546 (2013). It is noted here that the IMGT/LIGM-DB is the IMGT comprehensive database of immunoglobulin (IG) and T cell receptor (TR) nucleotide sequences from human and other vertebrate species; see Nucleic Acids Res. 2006 Jan. 1; 34(Database issue):D781-4.

In order to maintain the binding properties of the parental murine antibody, the following two back mutations were introduced into the framework region of the variable humans. In the variable domain of the heavy chain of the human germline of IGHV3-11*06 the serine at position 49 was back-mutated to an alanine that is present in the murine antibody 10B3 (see also FIG. 10C in which the alanine residue at position 49 is highlighted in bold and italics). In the variable domain of the light chain sequence of IGKV3-20*02 the phenylalanine at sequence position 72 of the human germline sequence was back-mutated to a tyrosine residue that is present at this sequence position in the murine antibody 10B3 (see also FIG. 10D in which the tyrosine residue at position 72 is highlighted in bold and italics).

Example 3: Production of Recombinant Antibody Molecules and Off-Target T Cell Activation by Different PSMAxCD3 Antibodies For construction of recombinant bispecific antibody molecules, the variable domains of the PSMA antibodies J591 and 10B3 were fused to human constant regions and variable regions of the CD3 antibodies OKT3 or UCHT1 in the following order. VL-CL for both, the Fabsc- and IgGsc-formats. Heavy chains were constructed as follows: VH-CH1-CH2mod-scFv(OKT3/UCHT1) for the Fabsc format, VH-CH1-CH2mod-CH3-scFv(OKT3/UCHT1) for the IgGsc-format (cf. also FIGS. 1A and 1). In these antibody molecules, the PMSA binding site is present as Fab fragment while the CD3 binding site is present as scFv fragment (cf.

again FIGS. 1A and 1*i*). To abrogate FcR-binding, glycosylation sites and the formation of disulfide bonds the following modifications were introduced into the hinge region and the CH2 domain of the Fabsc format (EU-index): C226S; C229S; E233P; L234V; L235A; AG236; D265G; N297Q; A327Q; A330S (see in this respect also International patent application WO 2013/092001). Modifications of the IgGsc formats were identical except for the two cysteine mutations at sequence positions 226 and 229 in the hinge region that are lacking in the IgGsc-format. The constructs were cloned in an expression vector derived from pcDNA3.1 (InVitrogen, Thermo Fisher) and transfected into Sp2/0 cells by electroporation as also described in International patent application WO 2013/092001. Antibody molecules were purified from the supernatants of transfected cells by affinity chromatography with kappaSelect (Fabsc) or Protein A (IGGsc) resins. Both affinity resins were purchased from GE Health Care Freiburg, Germany.

For characterization of the off-target T cell activation PBMC were incubated with the indicated antibody molecules of J519 and 10B3 in the absence and presence of SKW6.4 bystander lymphoma cells. After 2 days CD69 expression of CD4 T cells was analyzed by flow cytometry. To this end the PMBCs were incubated with detection antibodies directed to CD4 (FITC labeled clone HP2/6), CD8 (APC-labeled clone HIT8a) and CD69 (PE labeled clone FN50) to identify T cells expressing the activation marker CD69. Cells were analyzed using a FACS Canto II from BD Biosciences.

Figure 2:
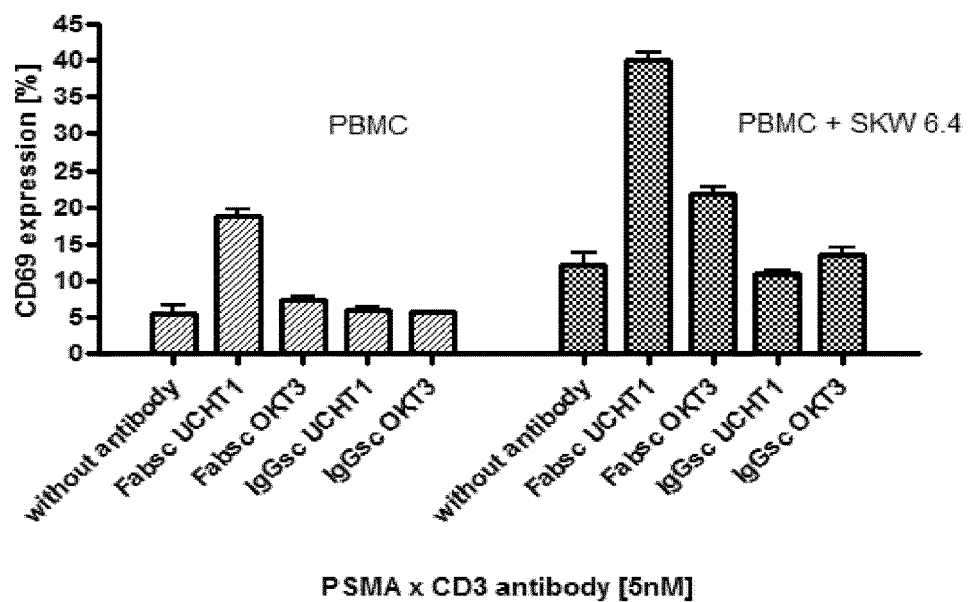
FIG. 2 depicts off-target T cell activation by different PSMAxCD3 antibodies. PBMC were incubated with the indicated antibodies in the absence and presence of SKW6.4 lymphoma cells. After 3 days CD69 expression of T cells was analyzed by flow cytometry.

Conclusion: As shown in FIG. 2 (which shows the results for the bispecific antibody molecules containing the variable domains of the antibody J519), the Fabsc antibody molecule containing the scFv fragment of the CD3 binding antibody UCHT1 induces T cell activation in the absence of PSMA expressing cells (off-target T cell activation) whereas the IgGsc antibody molecule that comprising the same target, i.e. PMSA binding site, and effector antibody binding site (i.e. the scFv fragment of the CD3 binding antibody UCHT1) does not.

Figure 3A:
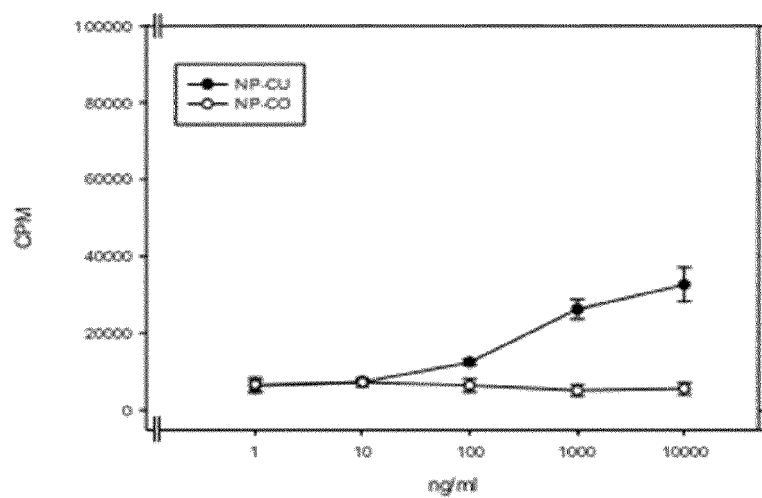
FIGS. 3A-3C show T cell activation, which was assessed by $^3$H thymidine uptake.
Figure 3B:
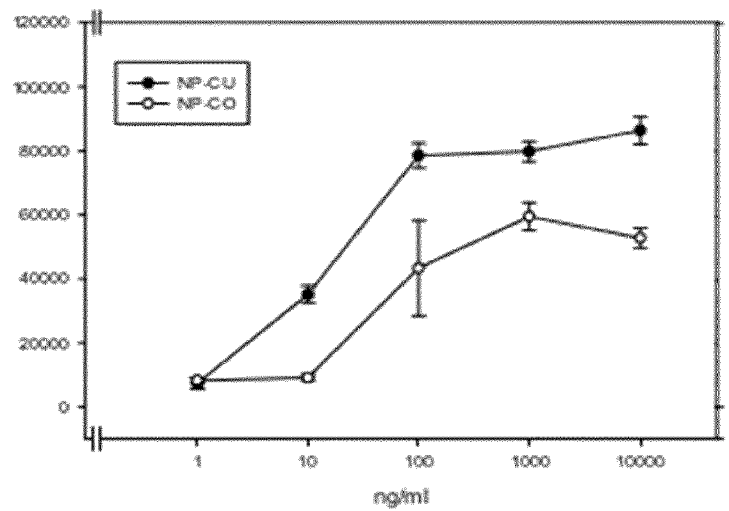
Figure 3C:
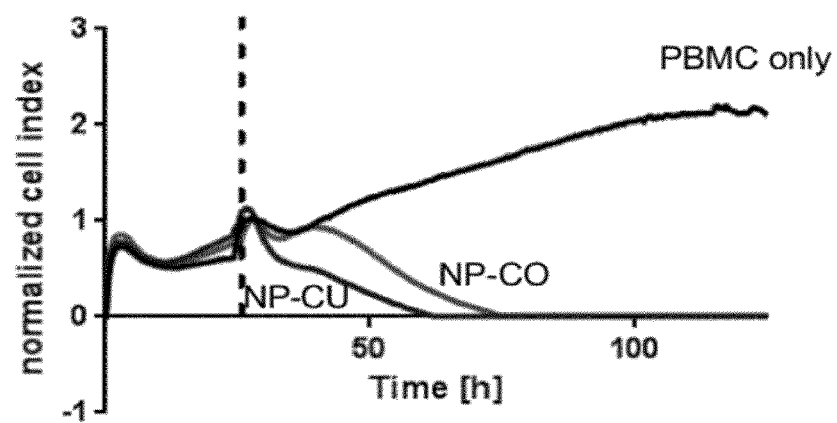

Example 4: On-Target T Cell Activation with PSMAxCD3 Antibodies in the Fabsc-Format In FIGS. 3A-3C T cell activation was assessed by $^3$H thymidine uptake. In FIG. 3A off-target T cell activation is shown for comparison. In FIG. 3C lysis of PSMA expressing target cells by activated T cells is demonstrated by an Xelligence cytotoxicity assay. For the $^3$H-thymidine uptake assay PBMCs ($20^5$/well) were seeded in triplicates in 96 well plates and incubated with various concentrations of bispecific antibody molecules with (FIG. 3B) or without (FIG. 3A) irradiated (100 Gy) PSMA expressing 22RV1 cells ($10^5$/well). After 72 hours, cells were pulsed for another 20 hours with $^3$H-thymidine (0.5 µCi/well) and harvested on filtermats. The incorporated radioactivity was determined by liquid scintillation counting in a 2450 Microplate counter (Perkin Elmer).

For the Xelligence assay 50 µl of culture media were added to 96 well E-plates (Roche) to determine background values. Subsequently, target cells (22RV1) were seeded at a density of 40.000 cells per well. Over the next 20-24 hours cells were allowed to adhere to the wells. Then, PBMCs, isolated by density gradient centrifugation, were added to the target cells. The effector to target ratio (E:T) was 5:1 and the bispecific antibody concentration was 1 µg/ml. The impedance was monitored every 15 minutes for several days as a measure for the viability of the adherent target cells.

Conclusion: The bispecific PSMAxCD3 antibody containing OKT3 (NP-CO) is slightly less effective in mediating "on target" T cell activation and target cell killing as the reagent containing UCHT1 (NP-CU).

Example 5: Multimerization and Aggregation of Different Bispecific Antibody Formats In FIG. 4A and FIG. 4B antibody molecules with FLT3xCD3-specificity are compared (Fabsc- vs bscc-format), while in FIG. 4C-F those antibody molecules with PSMAxCD3-specificity are compared (Fabsc- vs- IgGsc-format). The gel filtration that was used to analyze the multimerization behavior was performed on Superdex S200 columns.

Figure 4D:
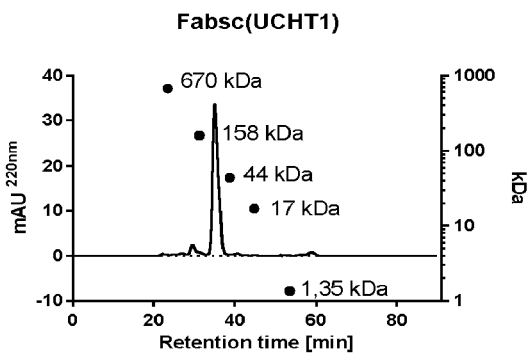
Figure 4E:
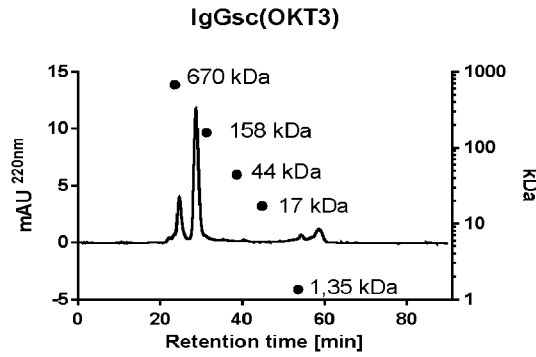
Figure 4F:
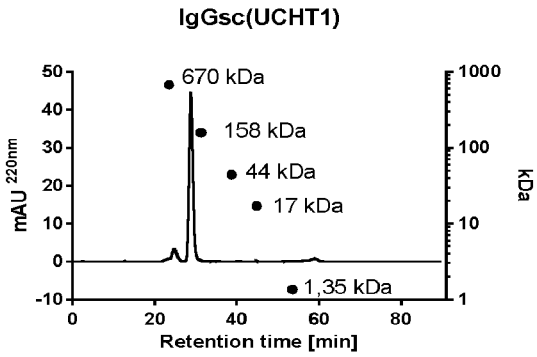

Conclusions: (i) As shown in FIG. 4B, antibodies within the bssc format (see FIG. 1C for the bispecific single chain format used in the experiment of FIG. 4B) have a marked tendency to form multimers and aggregates. This tendency is much lower in the case of the Fabsc- and IGsc-formats (FIG. 4A, FIGS. 4C-F). (ii) The moderate amount of multimers formed by the Fabsc/IgGsc constructs is higher for antibodies containing OKT3 (FIGS. 4C, 4E) compared to those comprising UCHT1 (FIGS. 4D, 4F). While the results shown in FIGS. 4C to 4F have been obtained with Fabsc/IgGsc molecules that contain the variable domains of the antibody J591 as PMSA binding site, the analogous behavior has been observed for the respective Fabsc molecules of the antibody 10B3 (data not shown).

Example 6: Binding of the PSMA-Antibodies J591 and 10B3 to PSMA-Expressing Cells Binding (FIG. 5A), lack of binding competition (FIG. 5B) and shift of the PSMA antigen upon antibody binding (FIG. 5C) was assessed by flow cytometry using PSMA-transfected Sp2/0 cells. To this end different α-PSMA antibodies were incubated with these cells in 96-well plates for 30-45 min at 4° C. Cells were then washed and incubated with a PE-conjugated goat-anti-mouse F(ab)$_2$ fragment (FIGS. 5A, 5C) (Jackson ImmunoResearch) or a PE-goat-anti-human FC-γ specific fragment (Jackson ImmunoResearch) (B). Cells were analyzed on a FACSCalibur (BD Biosciences). In FIG. 5B it is demonstrated that the chimeric (ch) PMSA binding antibody J591, specifically detected by a goat anti human secondary antibody, was out-competed by murine (mu) antibody J591 but not the murine antibody 10B3, i.e. an antibody of the present invention. For the determination of antigen shift (FIG. 5C) PSMA expressing cells were incubated with the indicated antibodies at the beginning of the experiment and again after 24 hrs and before FACS analysis with a saturating amount (10 µg/ml) of the respective antibody. PSMA expression by untreated cells served as a reference (100% PSMA expression)

Conclusions: (i) Binding of both antibodies, J591 and 10B3 is comparable, (ii) the antibodies do not cross-compete with each other, that is they bind to different epitopes and (iii) antigen shift induced by the 10B3 antibody is markedly reduced when compared to that exerted by the antibody J591.

Example 7: Cryostat Sections Stained with the PSMA Antibodies J591 and 10B3

Figure 6A:
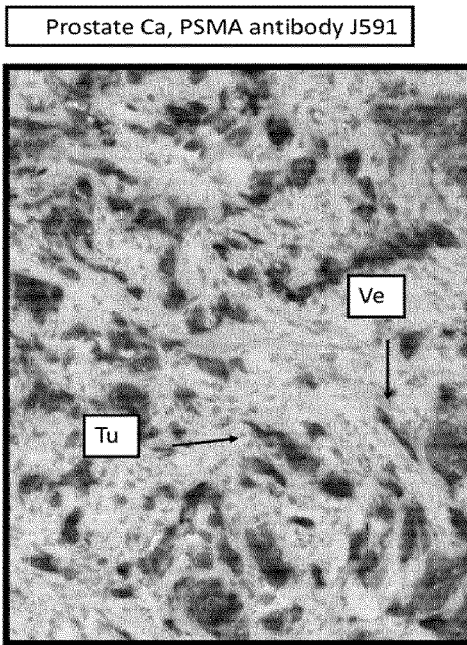
FIGS. 6A-6D show cryostat sections stained with the PSMA binding prior art antibody J591 and the 10B3 antibody of the invention.
Figure 6B:
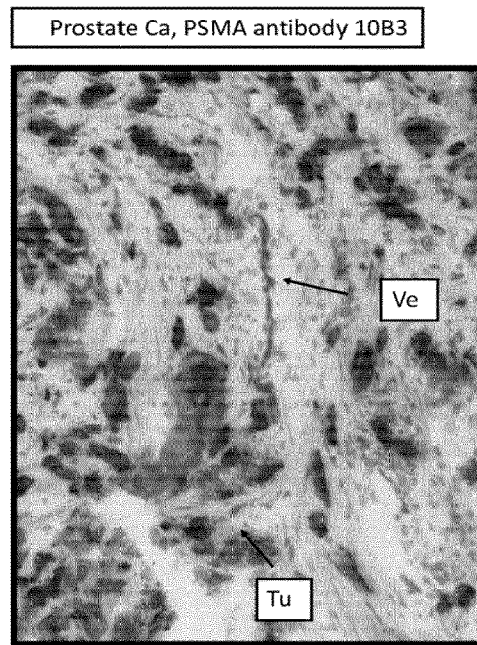
Figure 6C:
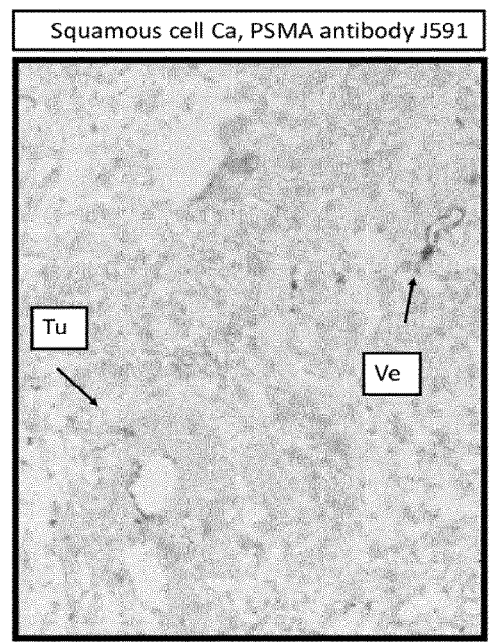
Figure 6D:
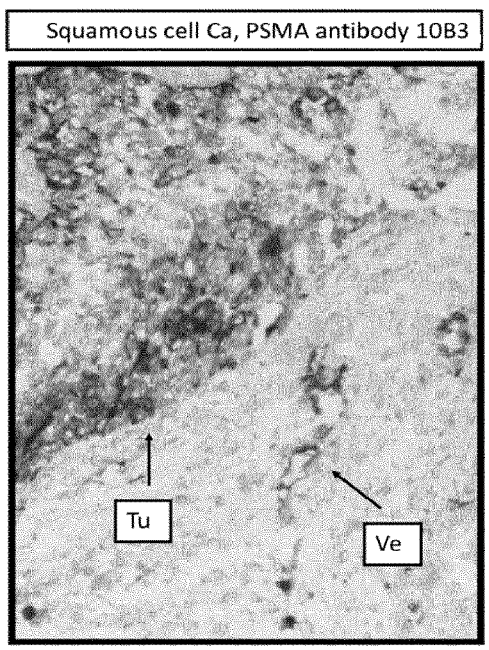

In FIGS. 6A, 6B a prostate carcinoma cell sample was stained with both antibodies while in FIG. 6C and FIG. 6D a squamous cell carcinoma sample was stained with both antibodies. In both experiments the staining was carried out in parallel and using a polymer system from Zytomed, Berlin, Germany (POLHRP-100). Arrows indicate tumor stroma (Tu) and blood vessels (Ve). Representative results from 9 of 10 prostate cancer samples and 7 of 10 squamous cell carcinoma samples are shown.

On a variety of different normal human tissues (obtained from BioCat, Heidelberg, Germany, T6234701-2) the staining pattern of the two antibodies was identical with the exception of a faint reactivity of the antibody 10B3 with epithelial cells in the skin.

Conclusions: (i) staining of prostate carcinoma samples and normal tissue is comparable with both antibodies, (ii) in squamous cell carcinoma samples the J5191 antibody stains only vascular cells whereas the antibody 10B3 stains vascular cells (more extensively than J591) and the tumor cells themselves.

Example 8: Binding of Humanized and Mouse 10B3 Antibodies

Figure 7:
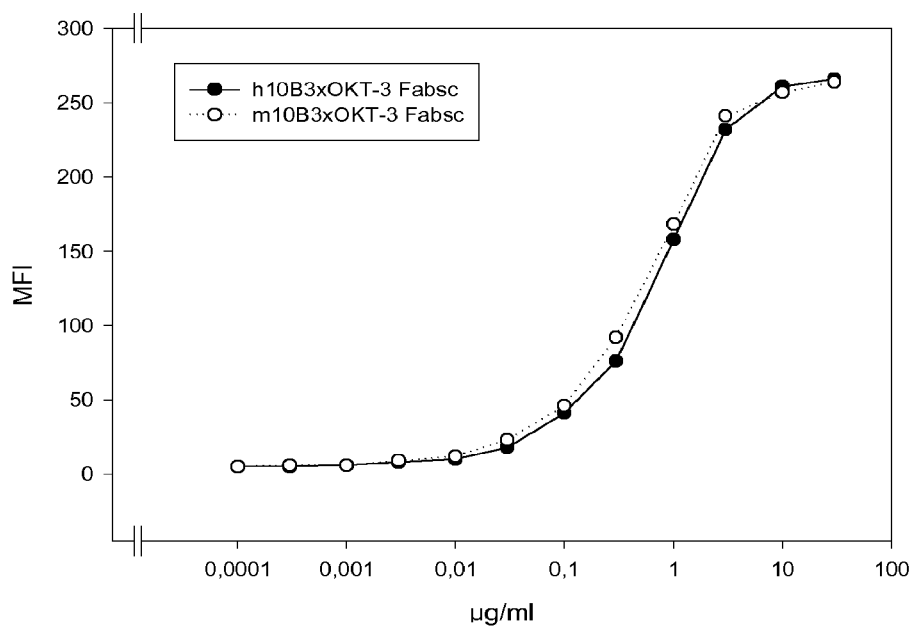
FIG. 7 shows the binding of humanized and mouse 10B3 antibody molecules. Bispecific Fabsc antibody molecules with PSMAxCD3 (10B3xOKT3)-specificity containing either the humanized, CDR-grafted (h10B3) variable domains or the mouse (m10B3) antibody variable domains were incubated with PSMA-expressing 22RV1 cells and analyzed by flow cytometry.

Bispecific Fabsc antibodies with PSMAxCD3 (10B3xOKT3)-specificity containing either the variable domains of the humanized, CDR-grafted (h10B3) or mouse (m10B3) antibody were incubated with PSMA-expressing 22RV1 cells and analyzed by flow cytometry (FIG. 7). To this end, the cells were incubated with the indicated antibodies in 96 well plates for 30-45 min at 4° C. Upon incubation cells were washed and incubated with a secondary PE-goat-anti-human FC-7 specific fragment (Jackson ImmunoResearch). Cells were analyzed on a FACSCalibur (BD Biosciences).

Conclusion: Binding of the mouse and humanized 10B3 versions (incorporated as a Fab moiety of the variable domains of 10B3 within a Fabsc-antibody molecule) to PSMA expressing cells is identical.

Example 9: Binding of Different PSMAxCD3 Antibodies to CD3

Jurkat cells were incubated with the antibody molecules (Fabsc (UCHT1)=a Fabsc molecule comprising the CD3 binding variable domains of the antibody UCHT1 and the variable domains of the antibody J591; IgGsc (UCHT1) =IgGsc molecule comprising the CD3 binding variable domains of the antibody UCHT1 and the variable domains of the antibody J591, Fabsc (OKT3)=a Fabsc molecule comprising the CD3 binding variable domains of the antibody OKT3 and the variable domains of the antibody J591, IgGsc (OKT3)=IgGsc molecule comprising the CD3 binding variable domains of the antibody OKT3 and the variable domains of the antibody J591) in 96 well plates for 30-45 min at 4° C. Cells were then washed and incubated with a Biotin-goat-anti-human IgG, F(ab')$_2$ fragment specific (Jackson ImmunoResearch) and Streptavidin-PE (Life Technologies). Cells were analyzed on a FACSCalibur (BD Biosciences).

Figure 8:
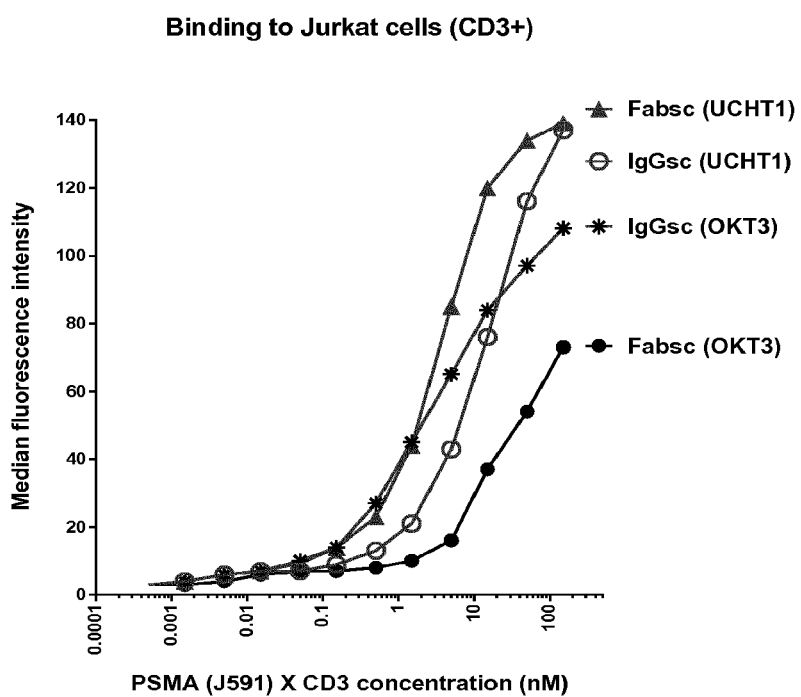
FIG. 8 depicts binding of the CD3-targeting part of different PSMAxCD3 antibodies. CD3-positive Jurkat cells were incubated with the indicated antibodies and analyzed by flow cytometry.

Conclusion: As shown in FIG. 8, avidity to CD3 is highest for the Fabsc-antibody containing UCHT1, lowest for that containing OKT3. Within the IgGsc format the UCHT1 construct loses—the OKT3 construct gains avidity. Since the avidity to of the bispecific antibody molecules to CD3 is obviously solely dependent on the CD3 binding (site), it is to be assumed that the ranking of the avidity of bispecific antibody molecules that contain the binding site of the antibody 10B3 will be the same as determined here using the variable domains of the antibody J591 as representative PMSA binding site (target binding site).

Example 10: Cytolytic Activity of the Different PSMA Antibodies

PSMA expressing 22RV1 prostate carcinoma cells were incubated with PBMCs and the indicated bispecific PSMAxCD3 antibody molecules (Fabsc (UCHT1)=a Fabsc molecule comprising the CD3 binding variable domains of the antibody UCHT1 and the variable domains of the antibody J591; IgGsc (UCHT1)=IgGsc molecule comprising the CD3 binding variable domains of the antibody UCHT1 and the variable domains of the antibody J591, Fabsc (OKT3)=a Fabsc molecule comprising the CD3 binding variable domains of the antibody OKT3 and the variable domains of the antibody J591, IgGsc (OKT3)=IgGsc molecule comprising the CD3 binding variable domains of the antibody OKT3 and the variable domains of the antibody J591) at a PBMC:target ration of 5:1. The viability of the adherent target cells was assessed using an Xelligence system as described in Example 4. The effector to target ratio (E:T) was 5:1 and the concentration of antibodies was set to 5 nM.

Representative results of one out of four different experiments with PBMCs of different healthy volunteers are shown in FIG. 9.

Conclusion: The ranking of lytic activity is: Fabsc (UCHT1)~IgGsc (UCHT1)>Fabsc (OKT3)>IgGsc (OKT3). Since the lytic activity of the bispecific antibody molecules is dependent on the CD3 binding (site), it is to be assumed that the ranking of the lytic activity of bispecific antibody molecules that contain the binding site of the antibody 10B3 will be the same as determined here using the variable domains of the antibody J591 as representative PMSA binding site (target binding site).

Example 11: Therapeutic Effect of PSMAxCD3 IgGsc (CC-1) In Vitro

Figure 15A:
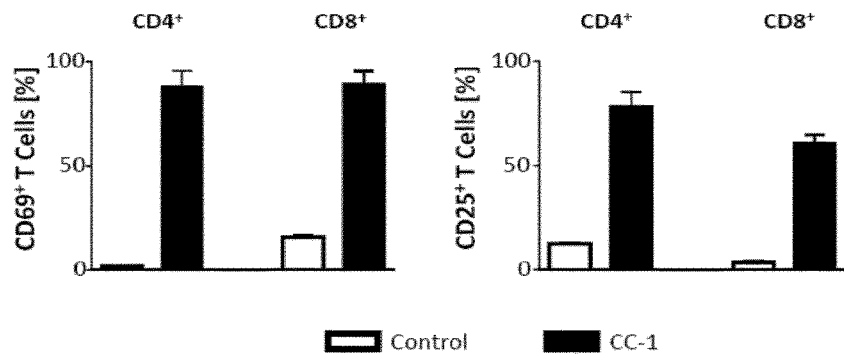
Figure 15B:
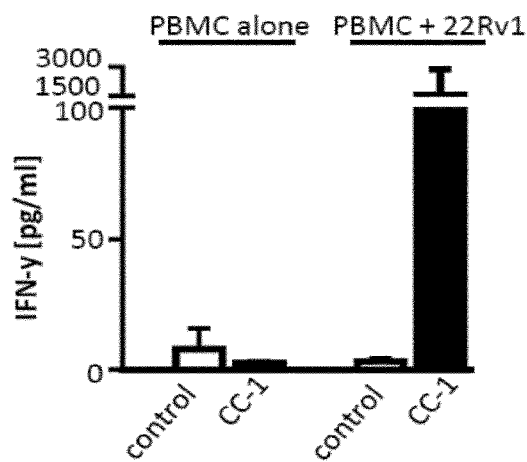
Figure 15C:
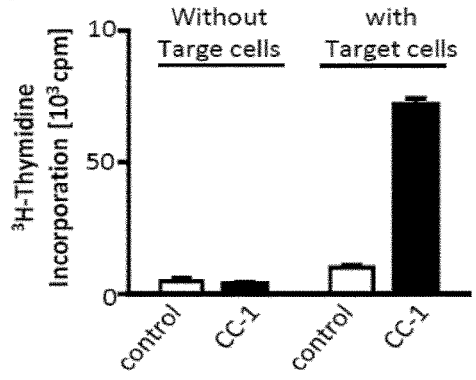
Figure 15D:
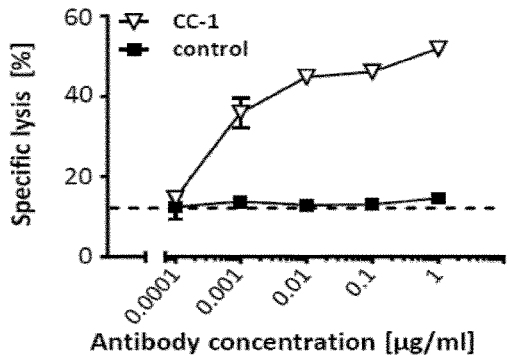

PSMAxCD3 (h10B3xUCHT1)-IgGsc (CC-1) bispecific antibody of the invention and a control bispecific antibody (NG2xCD3) were incubated with or without tumor cells (22Rv1 cells, human prostate carcinoma cells; see Sramkoski R M et al. In Vitro Cell Dev Biol Anim. 1999 July-August; 35(7):403-9.). CD4 and CD8 T cell activation was analyzed by FACS using CD69 and CD25 as cell surface markers after three days of incubation. Both T cell types were activated (FIG. 15A), and interferon gamma levels (FIG. 15B) and T cell proliferation increased (FIG. 15C). Chromium release assay (after 20 h E:T ratio 10:1) and FACS (over 72 h, E:T ration 1:1) furthermore showed a strong lysis of tumor cells using CC-1 (FIGS. 15D and E). Treatment with CC-1 of the invention also inhibited tumor growth in vitro. At an E:T ratio of 2:1, tumor cell growth in the presence of CC-1 is significantly impaired as analyzed with a Xelligence system (FIG. 15F left) and by visual inspection using a microscope (FIG. 15F right).

Conclusion: CC-1 induces a tumor cell restricted activation of T-cells and production of cytokines resulting in T cell proliferation and anti-tumor activity.

Example 12: Therapeutic Effect of PSMAxCD3 IgGsc (CC-1) In Vivo

Figure 16B:
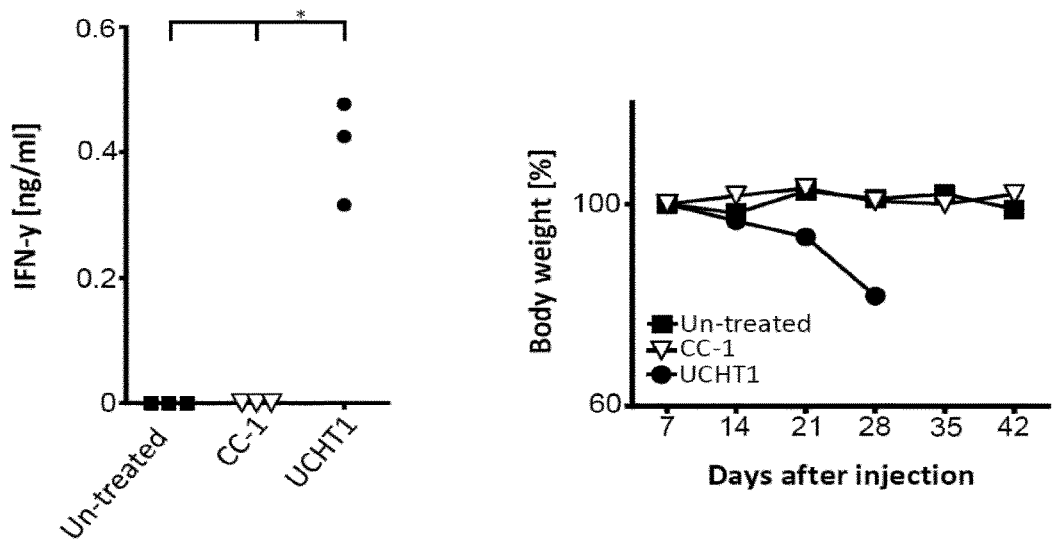
Figure 16C:
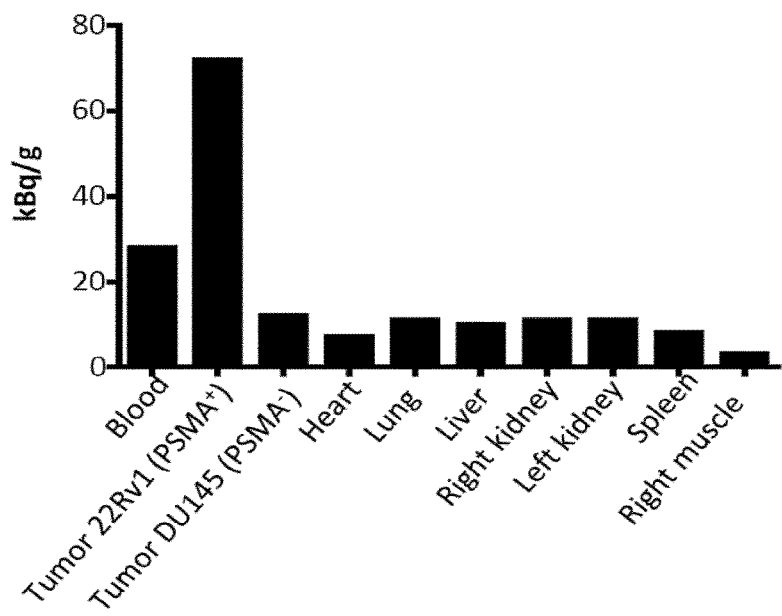
Figure 16D:
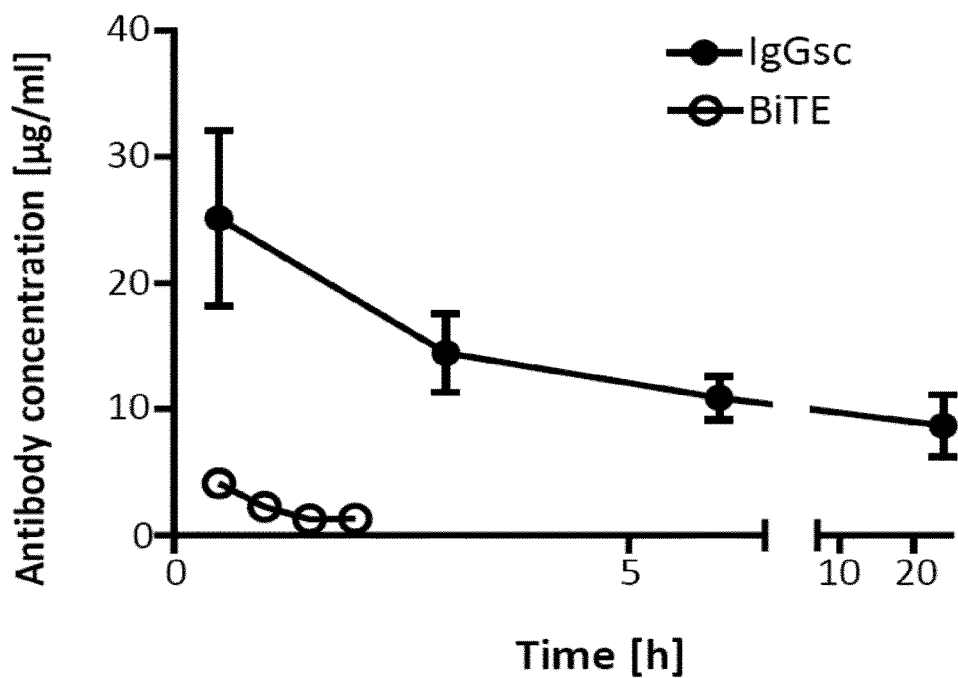

Next, CC-1 (the IgGsc bispecific antibody of the invention) was tested for anti-tumor activity in vivo in a mouse model. 1.5×10⁶ 22Rv1 cells were injected into NSG (NOD scid gamma, (NOD.Cg-PrkdC$^{scid}$ Il2rg$^{tm1Wjl}$/SzJ)) mice intravenously (n=4/group). After three days 3×106 human PBMC were injected and on day 3 and 5 10 μg CC-1 or PBS as negative control. After 8 days metastasis formation in the lung was analyzed using FACS. A significant reduction of the number of formed metastases was found in the CC-1 treated group (FIG. 16A). Then, NSG mice (n=3/group) were injected with 2×10⁷ PBMC per mouse and treated with "supratherapeutic" CC-1 doses at 2×20 μg in an interval of 4 days and a control antibody (UCHT1 as positive control, which activates T cells unspecifically) or PBS as negative control. IFNgamma release and bodyweight as a marker of autoimmune activity was analyzed (FIG. 16B). CC-1 compared to UCHT1 did not induce IFNgamma production, and no reduction of bodyweight in CC-1 treated mice was observed, contrarily to the UCHT1 treated group. In another experiment NOS/SCID mice were injected with 22Rv1 cells (PSMA positive tumor cells) or with DU145 cells (PSMA negative human prostate tumor cells) and after establishment of tumors after 35 days, mice were treated with a radioisotope labeled CC-1 antibody (50 μCi) and sacrificed after 24 h to measure radioactivity in different organs. Only in tumors of 22Rv1 treated mice a significant increase of radioactivity could be observed (FIG. 16C). To test the difference of serum half-life of bispecific antibodies of the BiTE or IgGsc format of the invention, Balb/C mice were injected with 50 μg of either CC-1 (IgGsc format) or the BiTE format bispecific PSMAxCD3 antibody. Serum concentration was measured over time. Bispecific antibodies of the BiTE format were not detectable after 2-4 h of injection, whereas CC-1 was still detectable in the serum after 24 h (FIG. 16D). Therefore, the IgGsc format of the invention provides increased serum stability compared to other bispecific antibody formats.

Conclusion: CC-1 suppresses tumor growth in vivo without inducing any unspecific immune responses. CC-1 targets specifically PSMA expressing tumor tissue and has compared with other bispecific formats an increased serum half-life.

Example 13: Comparison of UCHT1 and OKT3

To further elucidate the herein shown supremacy of UCHT1 over OKT3 as CD3 binding site in the IgGsc bispecific antibody format (see above), Fab and IgG versions of both monospecific antibodies were tested in comparison. OKT3 and UCHT1 were purified by protein A affinity chromatography. Fab fragments were generated by pepsin digestion followed by reduction and modification of hinge region disulfide bonds as previously described (Jung et al. Target cell induced T cell activation with bi- and trispecific antibody fragments. Eur J Immunol 1991; 21,2431-2435). Fab fragments were purified by size exclusion chromatography on a Superdex S200 column.

Then CD3 expressing Jurkat cells were incubated with increasing concentrations of the indicated antibodies, a biotin labelled detection antibody (anti-human Fab) followed by PE conjugated streptavidin. Samples were then analysed by flow cytometry (table 1). Concentrations at which half maximal binding was observed are indicated (nM).

TABLE 1

Avidity of Fab and IgG Versions of anti-CD3 antibodies

|  | IgG | Fab |
|---|---|---|
| OKT3 | 0.3 nM | 23.7 nM |
| UCHT1 | 0.6 nM | 0.6 nM |

Figure 1B:
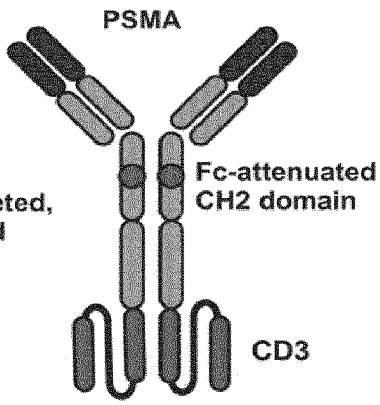
Figure 1C:
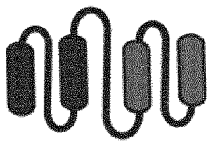

Conclusion:
OKT3 loses avidity if used as a univalent Fab fragment rather than a bivalent intact IgG molecule. In contrast the avidity of the UCHT1 fragment does not change. Without being bound to a theory, this points to a univalent binding of the intact UCHT1 antibody, the avidity of which is comparable to the bivalently binding OKT3 antibody. The marked difference in binding of the univalent Fab-fragments in favour of UCHT1 explains the corresponding difference in binding of the two antibodies within the Fabsc-format (FIG. 8, example 9). In this format the antibodies are present as a monovalent single chain molecule attached to the C-terminus of a targeting antibody (FIGS. 1A-1C). Univalent binding of UCHT1 also explains why this antibody loses— whereas OKT3 gains avidity if present within the IgGsc- rather than the Fabsc-format (FIGS. 1A-1C and FIG. 8, example 9).

Although in the IgG-format the avidity of the UCHT1 containing molecule (IgGsc-UCHT1) is comparable or even slightly lower than that of IgGsc-OKT3, the activity of IgGsc-UCHT1 against tumor cells is markedly—and unexpectedly—higher (FIG. 9, example 10).

In summary IgGsc-UCHT1 is a format with optimized properties combining low off target activation (FIG. 2, example 3) with optimal lytic activity against tumor cells (FIG. 9, example 10).

Example 14: UCHT1 is Effective in Other Bispecific IgGsc Format Antibodies

Figure 17A:
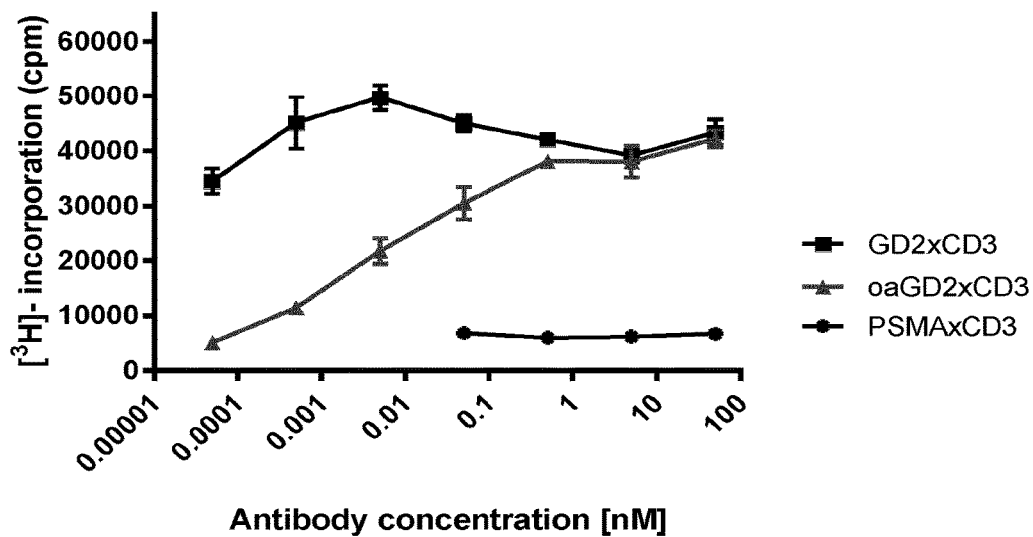
FIGS. 17A-17B show the T cell activation and tumor cell growth inhibition of non-PSMA targeting bispecific IgGsc antibodies with UCHT1 as anti CD3 specificity.

The preferred use of UCHT1 as anti-CD3 antibody in an IgGsc based antibody format was further tested for other non-PSMA specific antibodies. Irradiated M21 melanoma cells expressing the ganglioside GD2 as well as an O-acetylated form of this antigen (oaGD2) were incubated with peripheral blood mononuclear cells (PBMC) isolated from the peripheral blood of normal human donors and bispecific IgGsc antibodies with the indicated specificities. Parental monospecific antibodies used within these constructs were hu14.18 (anti-GD2), 8B6 (anti-oaGD2), J591 (anti-PSMA) and UCHT1 (anti-CD3), respectively. After 3 days T-cell activation was assessed using a ³H-thymidine incorporation assay. Further, M21 cells were incubated with PBMC and the indicated bispecific IgGsc antibodies (50 nM). Tumor cell growth was then monitored using an Xelligence system. A bispecific IgGsc antibody with an unrelated target specificity (MOPC) was used as a control.
Conclusion:
In the presence of tumor cells expressing GD2 and oaGD2 and bispecific antibodies targeting these antigens effective activation of T cells within the PBMC population was observed. A control antibody targeting PSMA was ineffective, since M21 do not express PSMA (FIG. 17A).

Figure 17B:
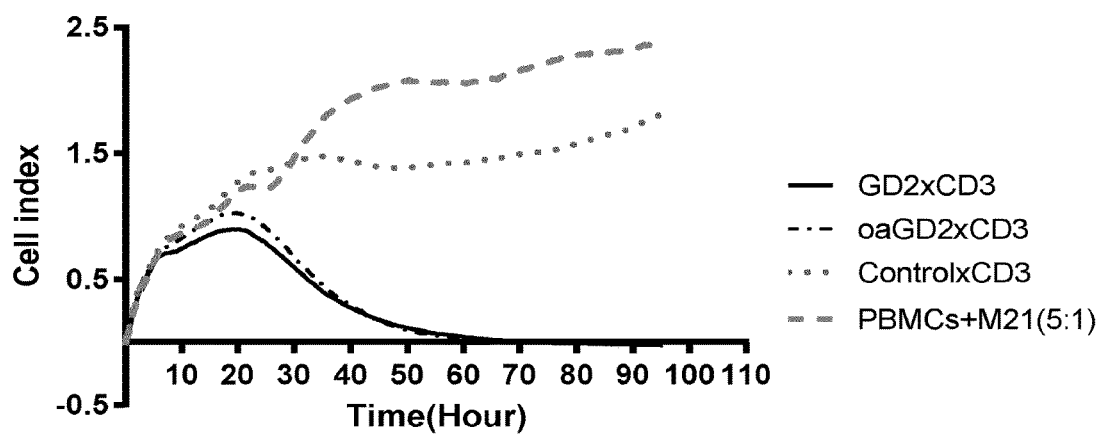

Bispecific IgGsc antibodies directed to GD2 or oaGD2 as target specificity and to CD3 as effector specificity effectively kill tumor cells expressing these antigens (FIG. 17B). The specific GD2- and CD3 antibodies used are listed in the legend to FIG. 17A.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

What is claimed is:

1. A tetravalent and homodimeric bispecific antibody molecule comprising two monomers, wherein each monomer comprises:
   i) an N-terminal Fab fragment comprising a variable region comprising a heavy chain variable domain and a light chain variable domain, wherein said variable region comprises a first binding site capable of binding to human prostate specific membrane antigen (PSMA); and
   ii) a C-terminal scFv fragment, comprising a heavy chain variable region and a light chain variable region of humanized UCHT1 comprising a second binding site, and
   wherein (i) and (ii) are connected by a CH2 and CH3 domain,
   wherein the heavy chain variable domain comprises a CDRH1 region as set forth in SEQ ID NO: 03 (GFTFSDFYMY), aCDRH2 region as set forth in SEQ ID NO: 04 (TISDGGGYTSYPDSVKG), and aCDRH3 region as set forth in SEQ ID NO: 05 (GLWLRDALDY); and
   wherein the light chain variable domain comprises a CDRL1 region as set forth in SEQ ID NO: 06 (SASS-SISSNYLH), a CDRL2 region as set forth in SEQ ID NO: 07 (RTSNLAS), and a CDRL3 region set forth in SEQ ID NO: 8 (QQGSYIPFT).

2. The tetravalent and homodimeric bispecific antibody molecule of claim 1, wherein at least one amino acid residue of the CH2 domain that is able to mediate binding to Fc receptors is lacking or mutated.

3. The tetravalent and homodimeric bispecific antibody molecule of claim 1, wherein the Fab fragment is not a Fab fragment of a non-humanized, chimerized or humanized J591 antibody.

4. The tetravalent and homodimeric bispecific antibody molecule of claim 1, wherein the heavy chain variable region and the light chain variable region of humanized UCHT1 comprise amino acid residues 471-714 of SEQ ID NO: 11.

5. The tetravalent and homodimeric bispecific antibody molecule of claim 1, wherein the heavy chain variable domain comprises the amino acid sequence as set forth in SEQ ID NO: 01 or 09, or wherein the light chain variable domain comprises the amino acid sequence as set forth in SEQ ID NO: 02 or 10.

* * * * *